United States Patent
Fujimoto et al.

(10) Patent No.: US 9,222,996 B2
(45) Date of Patent: Dec. 29, 2015

(54) NEEDLE PLACEMENT MANIPULATOR WITH TWO ROTARY GUIDES

(71) Applicants: Canon U.S.A., Inc, Melville, NY (US); Brigham and Women's Hospital, Boston, MA (US)

(72) Inventors: Kosuke Fujimoto, Kawasaki (JP); Yasumichi Arimitsu, Yokohama (JP); Nobuhiko Hata, Waban, MA (US); Sang-Eun Song, Boston, MA (US); Junichi Tokuda, Boston, MA (US)

(73) Assignees: The Brigham and Women's Hospital, Inc., Boston, MA (US); Canon U.S.A., Inc., Melville, NY (US)

( * ) Notice: Subject to any disclaimer, the term of this patent is extended or adjusted under 35 U.S.C. 154(b) by 251 days.

(21) Appl. No.: 13/837,806

(22) Filed: Mar. 15, 2013

(65) Prior Publication Data

US 2014/0275979 A1    Sep. 18, 2014

(51) Int. Cl.
*A61B 5/05* (2006.01)
*G01R 33/28* (2006.01)
*A61B 19/00* (2006.01)

(52) U.S. Cl.
CPC ............ *G01R 33/286* (2013.01); *A61B 19/201* (2013.01); *A61B 19/2203* (2013.01); *A61B 2019/4857* (2013.01)

(58) Field of Classification Search
CPC ............. A61B 19/201; A61B 17/3403; A61B 2017/3407; A61B 2017/3409; A61B 2019/5236; A61B 19/2203; A61B 2019/4857; G01R 33/286

USPC .................................................. 600/407–480
See application file for complete search history.

(56) References Cited

U.S. PATENT DOCUMENTS

| | | | |
|---|---|---|---|
| 4,841,967 A | 6/1989 | Chang et al. | |
| 5,196,019 A | 3/1993 | Davis et al. | |
| 5,201,742 A | 4/1993 | Hasson | |
| 5,280,427 A | 1/1994 | Magnusson | |
| 5,682,892 A | 11/1997 | Selder | |
| 5,957,934 A * | 9/1999 | Rapoport | 606/130 |
| 6,079,681 A | 6/2000 | Stern et al. | |
| 6,119,032 A | 9/2000 | Martin et al. | |
| 6,185,445 B1 | 2/2001 | Knuttel | |

(Continued)

FOREIGN PATENT DOCUMENTS

| CA | 2784988 A1 | 2/2013 |
|---|---|---|
| CN | 201642328 U | 11/2010 |

(Continued)

OTHER PUBLICATIONS

Stoianovici et al.,"Endocavity Ultrasound Probe Manipulators", IEEE/ASME Transactions on Mechatronics, Jun. 2013, pp. 914-921, vol. 18, No. 3.

(Continued)

*Primary Examiner* — Sanjay Cattungal
(74) *Attorney, Agent, or Firm* — Canon USA Inc. IP Division

(57) ABSTRACT

A needle placement manipulator includes, a pair of rotary guides arranged at a slanted angle with respect to each other, a needle holder which holds a needle along a needle holder axis, and a base body on which the guides are supported. The needle holder axis and each axis of the rotary guides cross at a single point located at or below the base body. The base body is configured to be attached to a patient or to an RF-coil.

30 Claims, 16 Drawing Sheets

(56) References Cited

U.S. PATENT DOCUMENTS

| | | | |
|---|---|---|---|
| 7,083,608 | B2 | 8/2006 | Tomita |
| 7,187,104 | B2 | 3/2007 | Yamamoto |
| 7,379,769 | B2 | 5/2008 | Piron |
| 7,766,878 | B2 | 8/2010 | Tremaglio, Jr. et al. |
| 7,824,417 | B2 * | 11/2010 | Magnusson et al. ......... 606/130 |
| 8,308,740 | B2 | 11/2012 | Tolley et al. |
| 2002/0019641 | A1 | 2/2002 | Truwit |
| 2005/0216026 | A1 | 9/2005 | Culbert |
| 2005/0261581 | A1 | 11/2005 | Hughes et al. |
| 2006/0149147 | A1 | 7/2006 | Yanof |
| 2006/0229641 | A1 * | 10/2006 | Gupta et al. ......... 606/130 |
| 2008/0161829 | A1 | 7/2008 | Kang |
| 2008/0167663 | A1 | 7/2008 | De Mathelin |
| 2009/0079431 | A1 * | 3/2009 | Piferi et al. ......... 324/318 |
| 2009/0234369 | A1 * | 9/2009 | Bax et al. ......... 606/130 |
| 2010/0010505 | A1 * | 1/2010 | Herlihy et al. ......... 606/130 |
| 2010/0082040 | A1 * | 4/2010 | Sahni ......... 606/130 |
| 2011/0190787 | A1 * | 8/2011 | Sahni ......... 606/130 |
| 2011/0251624 | A1 | 10/2011 | Yi |
| 2012/0022368 | A1 * | 1/2012 | Brabrand et al. ......... 600/427 |
| 2013/0267834 | A1 | 10/2013 | McGee |
| 2014/0052154 | A1 | 2/2014 | Griffiths et al. |
| 2014/0200445 | A1 | 7/2014 | Boezaart et al. |
| 2014/0275978 | A1 * | 9/2014 | Fujimoto et al. ......... 600/422 |

FOREIGN PATENT DOCUMENTS

| | | |
|---|---|---|
| EP | 2633882 A1 | 9/2013 |
| JP | 2004320846 A | 11/2004 |
| JP | 2005083961 A | 3/2005 |
| JP | 2008237971 A | 10/2008 |
| JP | 2013059588 A | 4/2013 |
| WO | 2009157007 A1 | 12/2009 |
| WO | 2011146018 A1 | 11/2011 |
| WO | 2011161218 A1 | 12/2011 |
| WO | 2013084107 A2 | 6/2013 |

OTHER PUBLICATIONS

Hata et al.,"MRI-Compatible Manipulator With Remote-Center-of-Motion Control", J Magn Reson Imaging, May 2008, pp. 1-12, vol. 27, No. 5.

Su et al.,"High-field MRI-Compatible Needle Placement Robots for Prostate Interventions: Pneumatic and Piezoelectric Approaches", Advances in Robotics and Virtual Reality, 2011, pp. 1-30.

M. Sam Eljamel, "Robotic Applications in Neurosurgery", Medical Robotics, 2008, pp. 41-66.

Song et al., "Biopsy Needle Artifact Localization in MRI-guided Robotic Transrectal Prostate Intervention," IEEE transactions on Biomedical Engineering, IEEE Trans Biomed Eng. Jul. 2012; pp. 1902-1911; 59(7).

Fischer et al., "MRI guided needle insertion—comparison of four techniques", In Annual Scientific Conference of the Society of Interventional Radiology, 2006 (Abstract).

Palmer, K., et al. "Development and evaluation of optical needle depth sensor for percutaneous diagnosis and therapies", Medical Imaging 2014: Image-Guided Procedures, Robotic Interventions, and Modeling, 2014, vol. 9036.

Song, S.E., et al., "Design Evaluation of a Double Ring RCM Mechanism for Robotic Needle Guidance in MRI-guided Liver Interventions", International Conference on Intelligent Robots and Systems, Nov. 3-7, 2013, pp. 4078-4083, Tokyo, Japan.

* cited by examiner

FIRST CONE OF ACCEPTANCE

SECOND CONE OF ACCEPTANCE

FIRST AND SECOND CONE OF ACCEPTANCE

VIEW FROM DIRECTION A

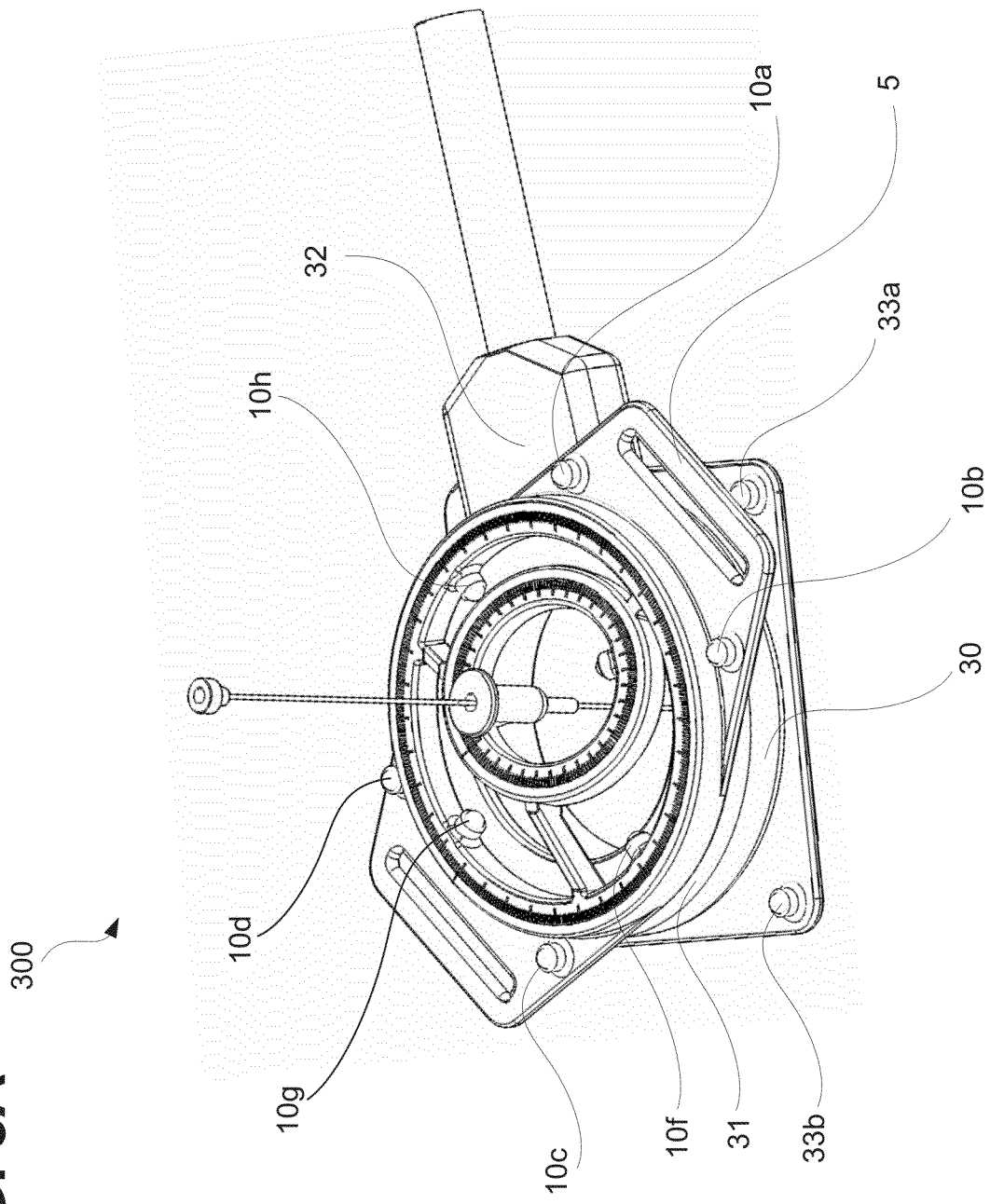

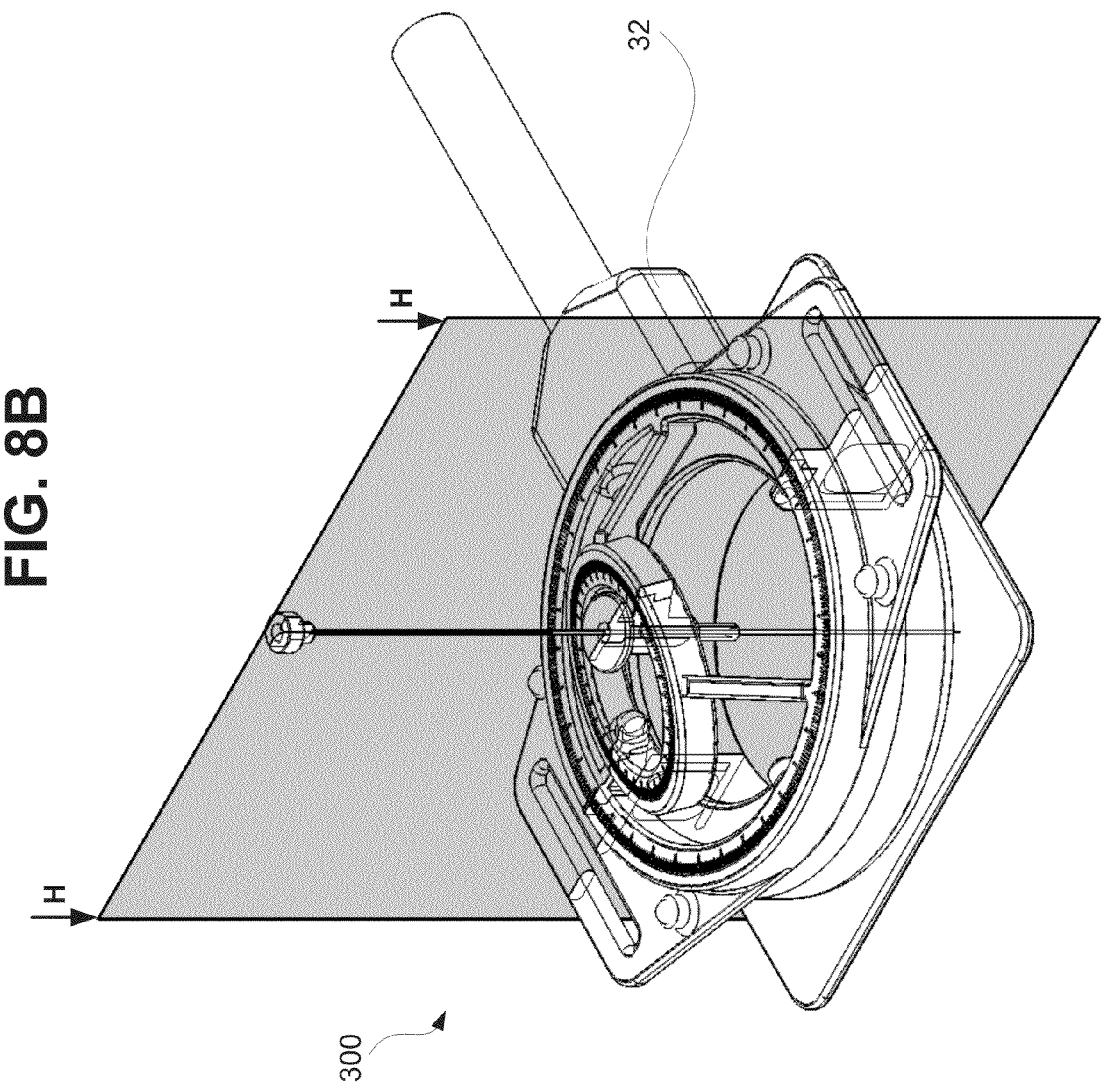

NEEDLE PLACEMENT MANIPULATOR WITH TWO ROTARY GUIDES

BACKGROUND

1. Field

The disclosure of this application relates generally to medical devices, and in particular it relates to a needle placement manipulator with two rotary guides slanted with respect to each other, and to a needle guidance system equipped with the needle placement manipulator.

2. Related Art

The use of imaging modalities, such as ultrasound, mammography, computed tomography (CT), Magnetic Resonance Imaging (MRI) and the like, to assist in identifying and treating abnormalities within the body of a patient, has gained increased acceptance in the medical field. The above-named and other imaging modalities generally provide good contrast between different soft tissues of the body. Thus, many of these techniques are being used to depict the boundaries of damaged tissue within healthy tissue for accurate identification and treatment. Advanced diagnostic procedures, however, require further validation and refinement in localization of damaged tissue. This further validation and advanced localization can be performed by needle biopsy procedures. To help define the boundaries of damaged tissue within healthy tissue with greater accuracy, needle guidance systems have been proposed.

A non-patent literature article entitled "MRI Guided Needle Insertion—Comparison of Four Techniques", by Fisher et al., describes four techniques for needle placement: 1) image overlay that projects an MR image and virtual needle guide on the patient, 2) biplane laser with needle trajectory marked by intersecting transverse and oblique sagittal lasers, 3) handheld protractor with pre-angled guide sleeve, and 4) freehand insertion. Conventionally, all of these techniques have required removing the patient out the imaging modality for needle insertion.

In the medical environment, it is necessary to position a needle tip precisely inside tissue or a specific organ for accurate diagnosis or minimal invasive therapy. Biopsy, ablation, cryotherapy, aspiration and drug delivery are examples that require high precision needle placement. Prior to a percutaneous incision, a target area of interest (e.g., tumor, nodule, etc.) is confirmed by means of non-invasive imaging with MRI, ultrasound or other imaging modality. Once the target area of interest is positively determined, the clinician decides an entry point, inserting direction and depth to be reached by the needle based on experience. This process often requires a lengthy trial and error routine, which can be deleterious to the patient. Accordingly, in the last few decades there has been an increased interest in the development of needle guiding systems that can improve accuracy of needle positioning, minimize patient discomfort, and shorten time of operation.

In the realm of needle guiding systems having a handheld protractor with pre-angled guide sleeve, US Patent Application Publication 2011/0190787 disclosed by Hirdesh Sahni (herein "Sahni") is an example. Sahni describes an "IMAGE GUIDED WHOLE BODY STEREOTACTIC NEEDLE PLACEMENT DEVICE with FALLING ARC". In Sahni's system, the device may be compatible with both CT and MRI modalities, but the patient has to hold the breath while the needle is being passed into regions that move on respiration. The device can be placed on the skin or on near an exposed organ of a patient, but its function can be jeopardized by movement.

In the realm of modality-guided needle placement systems, US Patent Application Publication 2006/0229641 disclosed by Rajiv Gupta et al., (herein "Gupta") is an example. Gupta describes a "GUIDANCE AND INSERTION SYSTEM", in which the insertion angle of the needle is guided by two arc-shaped arms which are driven by motors respectively attached at the axis of each arm. The device can be configured for use with an imaging apparatus, such as CT scanner, to allow the device and tool to be operated while viewing the device positioned in relation to a target surgical site. The device can be placed on a patient's skin and fastened by belts. The device can passively compensate for patient's movement.

In MRI-guided percutaneous interventions, accurate needle placement is of great concern and of considerably more difficulty that in needle placement systems for other modalities, such as CT or ultrasound. Unlike other modalities, MRI makes use of the property of nuclear magnetic resonance (NMR) to image nuclei of atoms inside the body. To that end, during an MRI scan, a patient is disposed within a powerful magnet where a large magnetic field is used to align the magnetization of atomic nuclei in the patient's body, and a radio frequency (RF) pulse is applied to alter the linear magnetization of the atomic nuclei. This causes the atomic nuclei to absorb energy from tuned radiofrequency pulses, and emit radiofrequency signals as their excitation decays. These signals, which vary in intensity according to nuclear abundance and molecular chemical environment, are converted into sets of tomographic (selected planes) images by using field gradients in the magnetic field, which in turn permits 3-dimensional (3D) localization of the point sources of the signals (or damaged tissue). More specifically, the detected signals are used to construct 2D or 3D MRI images of the scanned area of the body.

In an MRI-guided needle placement system, therefore, it is preferred that the entire positioning system consists essentially of non-magnetic materials such that there is no danger of impairing the homogeneity of the magnetic field within an examination volume. In addition, in order to track spatial positioning of the needle with respect to the guiding system, it is necessary to provide a marking point, such as a MR measurable fiduciary mechanically rigidly connected to the guiding system. In this manner, the position of the manipulator itself can be determined via MR measurement. U.S. Pat. No.: 6,185,445 to Knuttel discloses and example of such system.

Shortcomings of conventional technology include: 1. Rigidity of the guide is required to insert a needle with accurate position and posture. But rigidity of arc-shaped arm is low, and in particular rigidity of arc-shaped guides including attached motor is also low. 2. Arc-shaped arms provide visibility, so that a clinician can see the needle entry point, but opening is too small to access the entry point.

SUMMARY

According to at least one embodiment of the present application, a needle placement manipulator includes, a pair of rotary guides arranged at a slanted angle with respect to each other, a needle holder which holds a needle along a needle holder axis, and a base body on which the guides are supported. The needle holder axis and each axis of the rotary guides cross at a single point located at or below the base body. The base body is configured to be attached to a patient or to an RF-coil.

Further features of the present invention will become apparent from the following description of exemplary embodiments with reference to the attached drawings.

BRIEF DESCRIPTION OF DRAWINGS

FIG. 8A illustrates a perspective view of needle manipulator attached to an RF-coil, according to third embodiment; FIG. 8B illustrates a sectional cut along vertical plane H-H of the needle manipulator attached to an RF-coil;

DETAILED DESCRIPTION

Figure 1:
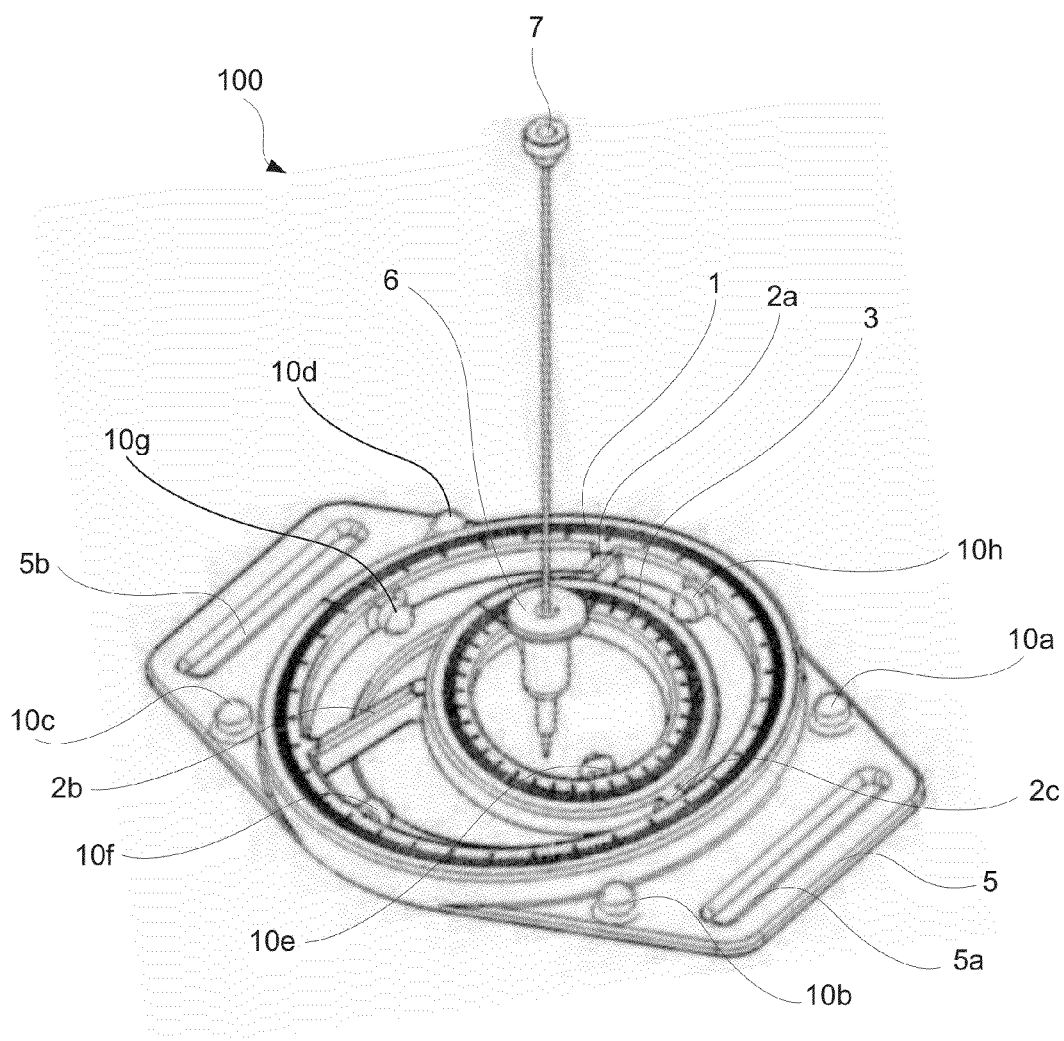
FIG. 1 illustrates a needle placement manipulator according to a first embodiment.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage device such as a magnetic or optical disk and disk drive for storing information and instructions, an optional user output device such as a display device (e.g., a monitor) for displaying information to the computer user, an optional user input device including alphanumeric and function keys (e.g., a keyboard) for communicating information and command selections to the processor, and an optional user input device such as a cursor control device (e.g., a mouse) for communicating user input information and command selections to the processor.

As will be appreciated by those skilled in the art, the present examples may be embodied as a system, method or computer program product. Accordingly, some examples may take the form of an entirely hardware embodiment, and entirely software embodiment (including firmware, resident software, micro-code, etc.) or an embodiment combining software and hardware aspects that may all generally be referred herein as a "circuit", "module" or "system". Further, some embodiments may take the form of a computer program product embodied in any tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Exemplary embodiments will be described below with reference to the several drawings, where like reference numerals refer to like parts.

<First Embodiment>

Figure 2A:
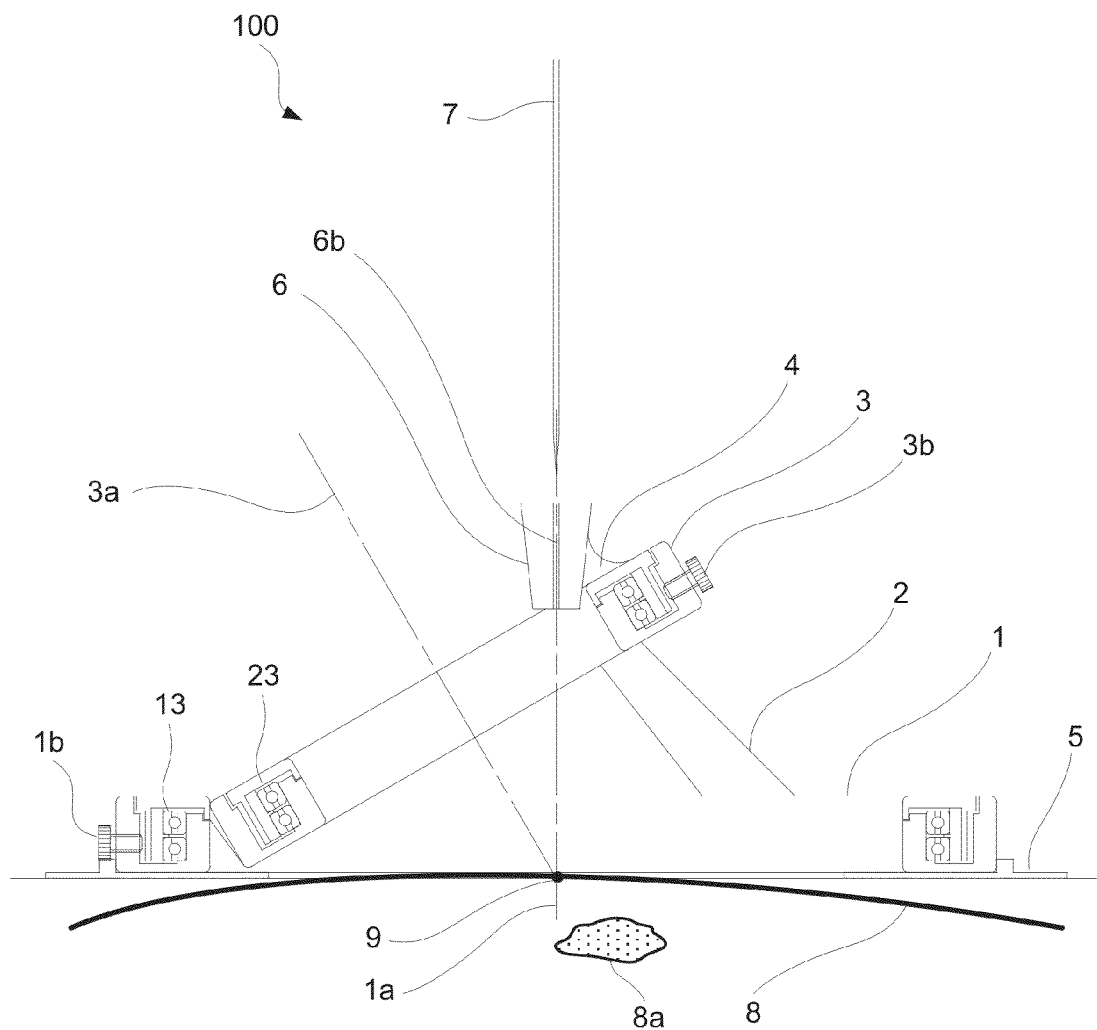
FIGS. 2A and 2B illustrates cross-sectional views of the needle placement manipulator according to the first embodiment.
Figure 2B:
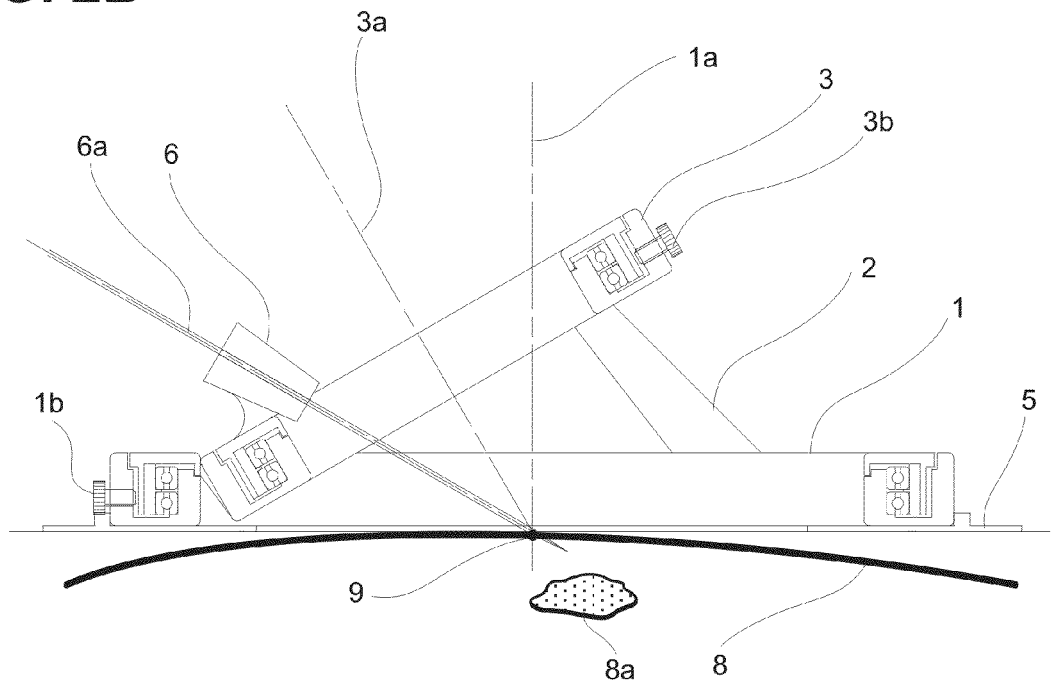

The first embodiment of the present invention is directed to a solution for the issues mentioned above. FIG. 1 is a perspective view of a needle placement manipulator 100 in accordance with the first embodiment. FIGS. 2A and 2B are sectional views of the needle placement manipulator at different operating positions.

As illustrated in FIG. 1, according to the first embodiment, a needle placement manipulator 100 includes two circular ring-shaped rotary guides (hereinafter referred simply to as "rotary guides"), which are arranged in a slanted orientation with respect to each other atop a base body 5. Specifically, a first rotary guide 1 and a second rotary guide 3 are arranged in a slanted orientation with respect to each other. The two rotary guides 1 and 3 are supported by a base body 5. The base body 5 is preferably a non-magnetic structure configured to be mounted on a patient's skin 8. As discussed in more detail below, the base body 5 and certain other elements can be manufactured of disposable and recyclable materials, such as plastics and/or composites thereof. The first rotary guide 1 is supported by the base body 5 and connects to a first rotation body 2. The second rotary guide 3 is supported by the first rotation body 2 and connects to a second rotation body 4. The second rotation body 4 is configured to support a needle holder 6. The needle holder 6 has a thru hole 6b configured to guide a needle 7 therethrough. The needle holder 6 constrains the needle 7 to align to selected angle geometrically determined by rotation of the two rotary guides 1 and 3.

The first rotation body 2 in this embodiment consists of three pillars 2a, 2b and 2c. But it is not limited to this structure. The first rotation body 2 can be formed of other structures, for example, one pillar or plurality of pillars, or a shell structure or a shell structure with holes. Many other shapes and structures may be readily available to a person having ordinary skill in the art. Notably, however, when the rotation body 2 consists of one or at most three pillars, as illustrated in FIG. 1, an ample opening for viewing an incision point is advantageously provided. Similarly, the second rotation body 4 consists of one or more pillars connecting the needle holder 7 to the second rotary guide 3.

Each of the rotary guides 1 and 3 respectively includes a set of rotational devices 13 and 23, and a fixing element 1b and 3b. Rotational devices promote easy rotation of the rotary guides to a desired position; and the fixing elements hold the rotary guides fixed in the desired position to prevent movement during a needle incision operation. In this embodiment, fixing elements 1b and 3b are set screws, and the rotational devices 13 and 23 are mechanical bearings. In preparation for an incision operation, a clinician or an automated actuator manipulates at least one the two rotary guides (the guides can operate independently from each other) to rotate the needle holder 6 to a predetermined angle. Once the desired position is reached, the rotary guides are fixed by tightening the fixing elements (screws) 1b and 3b, so that the needle holder 6 is directed to a desired angle to reach a target tissue 8a under the patient's skin 8. In this embodiment, fixing means are set screws. Air-clutches also can be used as fixing means instead of screws. The air-clutch is rotation-free when air-pressure is supplied from an air-supply source like a compressed gas cylinder or a medical air supply outlet in the surgical room; and when the air-supply is shut, the air-clutch holds the rotation of the rotary guides fixed.

Referring back to FIG. 1, markers 10a, 10b, 10c, 10d, 10e, 10f, 10g and 10h are MRI-visible fiducial markers which are arranged at predetermined locations on the base body 5, and first rotary guide 1, and the second rotary guide 3. During an MRI-guided intervention, images of these markers are acquired by MRI-scanner to obtain the spatial position and posture of each of these parts. Slits 5a and 5b provided within the base body 5 are slits for a belt to fasten the manipulator to patient's body.

In this embodiment in FIG. 1, the base body 5 is fixed to patient's body by fastening belts. But fastening is not limited to the belts only. The manipulator can be fastened to a patient's body by bolts passing through slits 5a and 5b to be fixed to bone of patients, or adhered to the patient by adhesive tapes, suction cups, and so on. It is also can be fixed to patient's bed or floor by a passive arm which can hold its joints by air clutch.

As illustrated in FIG. 2A, the first rotary guide 1 rotates around a fixed rotational axis 1a. And the second rotary guide 3 rotates around a fixed rotational axis 3a. The term "fixed rotational axis", as used herein, means that the axis of rotation is fixed with respect to its corresponding rotating part. The needle holder 6 includes the thru-hole 6b through which a needle holder axis 6a passes longitudinally. The axis 1a of first rotary guide 1, the axis 3a of second rotary guide 3, and the axis 6a of the needle holder 6 are arranged to always cross at a single crossing point 9 located at the center of gravity of the base body 5. As used herein, the term "center of gravity" refers to the point at which all the surrounding weight is equal. That is, it is the point at which an object is in balance.

In operation, the direction of the needle is determined by two angles of the rotary guides 1 and 3 without changing the crossing point 9. In FIG. 2A, the needle holder axis 6a is substantially perpendicular to the base body 5, and thus also substantially perpendicular to the first rotary guide 1. It can be said therefore, that at a given first position the needle holder axis 6a can be made substantially perpendicular to the first rotary guide 1. In this first position, the needle holder axis 6a can be made to substantially coincide with the axis 1a. From this given first position, the needle holder axis 6a and consequentially the needle holder 6 can be moved to any position between the initial perpendicular position (FIG. 2A) and a maximum inclined position illustrated in FIG. 2B.

Figure 2C:
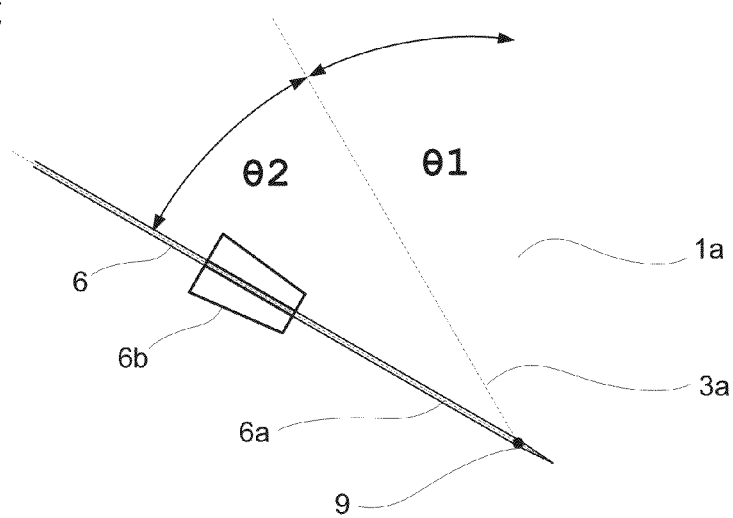
FIG. 2C illustrates an angular relationship between the rotational axes of rotary guides and a needle holder axis.

FIG. 2C illustrates the angular relationship between the rotational axis 1a of the first rotary guide 1, the rotational axis 3a of the second rotary guide 3 and the needle holder axis 6a of the needle holder 6. As illustrated in FIG. 2C, all of the axis 1a, 3a and 6a coincide and are fixed at the crossing point 9. Here, it should be understood that the rotational axis 1a of the first rotary guide 1 and the rotational axis 3a of the second rotary guide 3 are preferably fixed with respect to each other. However, the needle holder axis 6a of the needle holder 6 is not fixed with respect to the axis 1a, and thus the needle holder axis 6a can be positioned at a maximum inclination with respect to the axis 1a or at the same location as axis 1a.

In the position illustrated in FIGS. 2B and 2C, θ1 is the angle between the rotational axis 1a of the first rotary guide 1 and the rotational axis 3a of the second rotary guide 3; and θ2 is the angle between the rotational axis 3a of the second rotary guide 3 and the needle holder axis 6a of the needle holder 6, when the needle holder axis 6a is at its maximum inclined position. However, since the needle holder axis 6a can be moved, the needle holder axis 6a can be positioned at any angle between the first position (substantially perpendicular to the first guide 1) and the maximum inclined position at a maximum inclination angle θ3=θ1+θ2. The position of the needle holder 6 can be determined by the displacement of the needle holder axis 6a around the axis 3a and/or around the axis 1a of the first rotary guide 1.

Figure 3A:
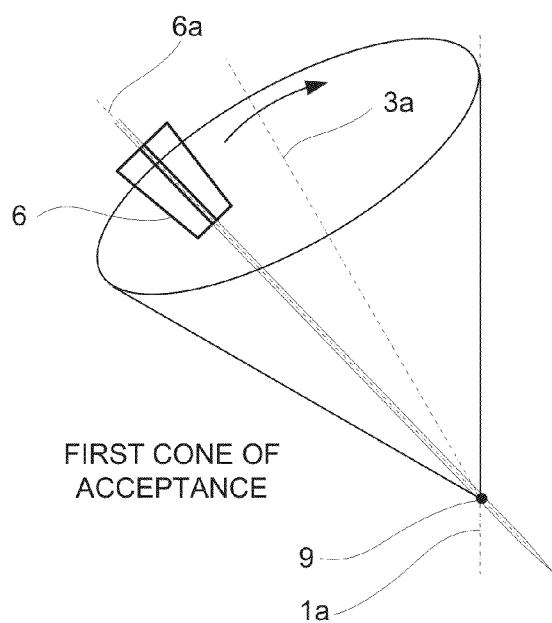
FIGS. 3A, 3B and 3C illustrate examples of needle insertion at a single crossing point with various angles of insertion.
Figure 3B:
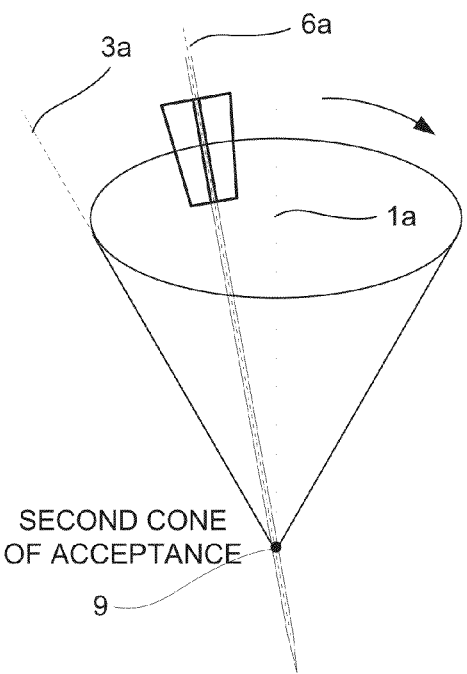

More specifically, as the second rotary guide 3 rotates around its rotational axis 3a, the needle holder axis 6a is displaced (travels) around a cone formed by the inner diameter of second rotary guide 3 and the crossing point 9. This cone will be referred to as a first cone of acceptance. FIG. 3B illustrates a position where the needle holder axis 6a has been displaced to a predetermined position around the circumference of the second rotary guide 3 from that shown in FIG. 2B. That is, as shown in FIG. 3B, the needle holder axis 6a has been displaced around the first cone of acceptance.

Similarly, as the first rotary guide 1 rotates around its rotational axis 1a, the axis 3a of the second rotary guide 3 is displaced (precesses) around the axis 1a. Since the axis 1a and axis 3a are fixed at the crossing point 9, the precession of axis 3a around the axis 1a defines another cone, which will be referred to herein as a "second cone of acceptance". The second cone of acceptance is formed by the circumference defined by axis 3a and the crossing point 9 with respect to the axis 1a, as the first rotary guide 1 rotates around its axis 1a.

Figure 3C:
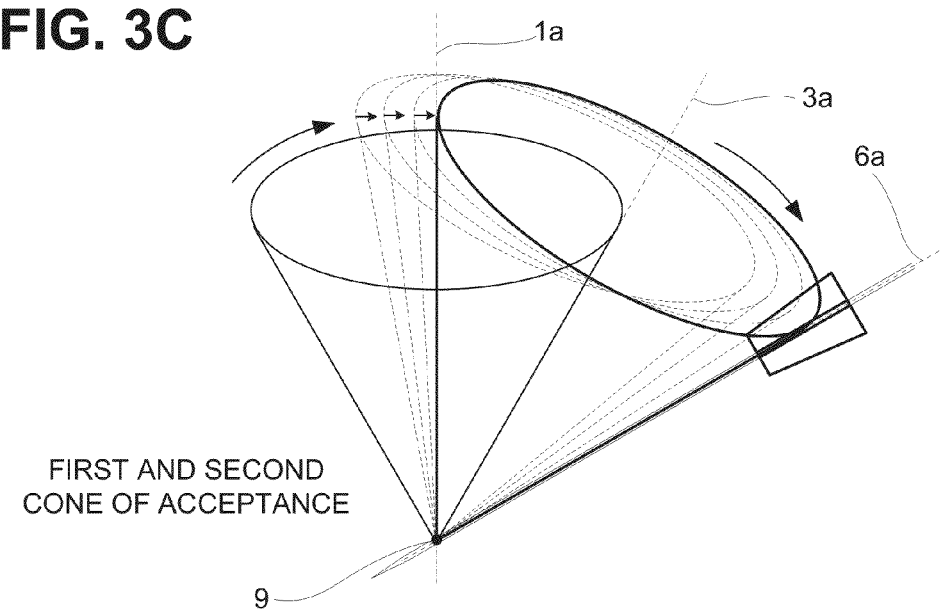
Figure 4A:
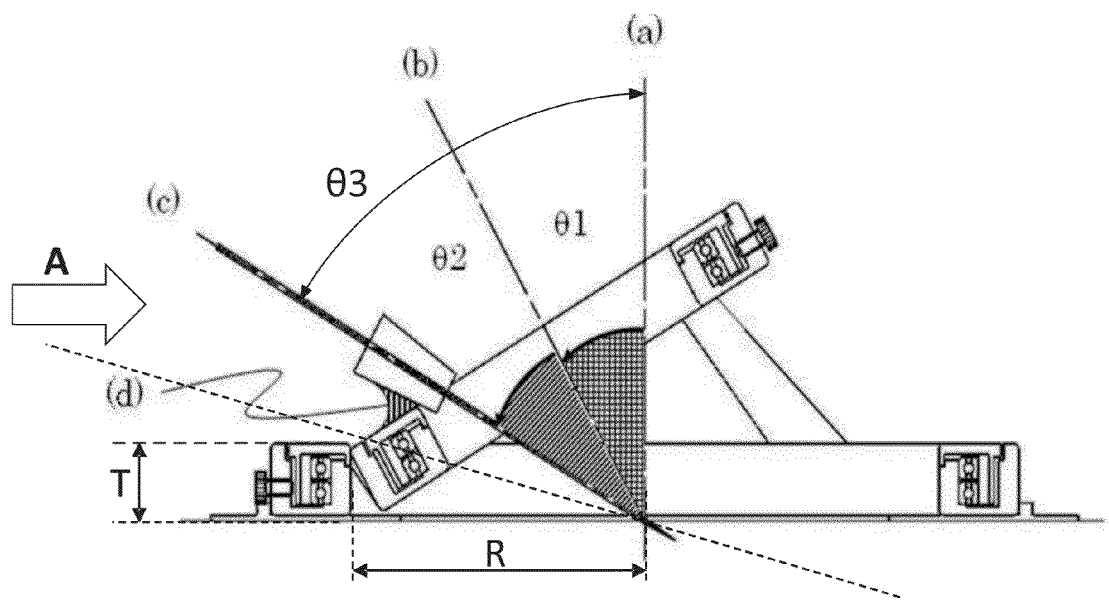
FIGS. 4A and 4B illustrate a maximum angle of inclination θ3 and optimal rotational space determined by the maximum angle of inclination θ3.

It should be recognized therefore, that needle placement can be effected at the fixed crossing point 9 from anywhere within the first cone of acceptance and/or the second cone of acceptance. FIGS. 3A, 3B and 3C illustrate in explicit detail some examples of needle insertion at crossing point 9 with various angles of insertion. In FIG. 3A, the first cone of acceptance is formed when the second rotary guide 3 rotates around its own axis of rotation 3a. In FIG. 4A, it is assumed that the first rotary guide 1 is fixed (does not rotate). In this assumed fixed position of the rotary guide 1, the needle holder 6 can be displaced (rotated) to point around the base on the first cone of acceptance, but one point of the needle holder axis 6a will be fixed at crossing point 9. Now it is assumed that the second rotary guide 3 stops rotating.

Turning now to FIG. 3B, the second cone of acceptance is formed when the first rotary guide 1 rotates around its own axis of rotation 1a. In FIG. 3B, it is assumed that that second rotary guide 3 is fixed (does not rotate). In the assumed fixed position of the second rotary guide 3, since the first rotary guide 1 is connected to the second rotary guide 3 via the rotation body 2 (pillars 2a-2c), the needle holder 6 can be displaced (rotated) to any point around the base of the second cone of acceptance, but the one point of the needle holder axis 6a will still remain fixed at crossing point 9. In this manner, the needle holder 6 can be positioned at any angle between the perpendicular position and the maximum inclined position.

FIG. 3C illustrates that both the first and second cones of acceptance can be used to position the needle holder 6 at a desired position and angle, while still maintaining one point of the needle holder axis 6a at the crossing point 9. More specifically, FIG. 3C illustrates that both the first rotary guide 1 and the second rotary guide 3 can be rotated simultaneously (or separately) around their corresponding axis 1a and 3a. In this manner, the second rotary guide 3 can rotate around its axis 3a and can precess around the axis 1a of the first rotary guide 1.

Therefore, arranging the crossing point 9 at the desired needle insertion point of the skin 8, allows a clinician to insert the needle 7 from any angle within an acceptance cones allowed by rotation of the rotary guides 1 and 3. In this manner, the target tissue 8a can be reached from different incision angles without changing the position of the inserting point. In addition, since the needle may be inserted from any angle within a cone of acceptance, with this manipulator a clinician can treat different regions of the tissue through only one insertion point on the patient's skin.

Figure 4B:
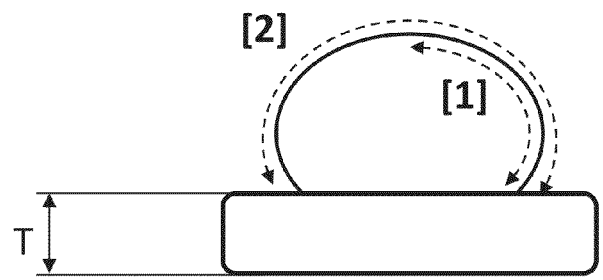

Referring now to FIGS. 4A and 4B a description is provided for a maximum angle of inclination θ3 and optimal use of rotational space determined by the maximum angle of inclination θ3. As illustrated in FIG. 4A, the actual usable space within the cones of acceptance for the needle holder 6 can be limited by the arrangement of the second rotary guide 3 in a slanted orientation with respect to the first rotary guide 1, above the base body 5. In FIG. 4A, T indicates the approximate height from a contact surface, e.g., a patient's skin 8 to an upper surface of the first rotary guide 1 above the base of base body 5 (i.e., above the needle incision point or crossing point 9); and R indicates the internal radius of the free space within the first rotary guide 1. Preferably, the point of needle incision or crossing point 9 is located at the geometric center at the bottom of the first rotary guide 1. In addition to the height of the first rotary guide 1, the needle holder 6 attached to the second rotary guide 3 occupies certain space above the base body 5, and the needle holder 6 requires a minimum of inclination with respect to the crossing point 9. When all of these parameters are taken into consideration, it is estimated that the needle holder axis 3a can have an maximum inclination θ3 defined by equation (1), as follows:

$$\theta 1+\theta 2 \leq \theta 3 = \pi/2 - \tan^{-1}(T/R) \quad (1)$$

Equation (1) provides the condition when all 360 degrees (a complete rotation) can be used for the second (tilted) rotary guide 3. However, to reach to the limit of equality of equation (1), the tilted second rotary guide 3 may need to be larger than the first rotary guide 1, and/or the tilted second rotary guide 3 may need to be positioned outside of the horizontal first rotary guide 1. Accordingly, a person of ordinary skill in the art will understand the embodiments disclosed herein can be modified to have the second rotary guide 3 outside the first rotary guide 1 and yet maintain a maximum inclination angle θ3 provided by equation (1).

Referring to FIG. 4B, it can be appreciated that the needle 7 extending along the needle holder axis 6a will encounter a physical obstacle in the horizontal first rotary guide 1. This limits the rotation of the second rotary guide 2 to a space [1] within a maximum allowable space [2]. Specifically, due to above-discussed actual size and arrangement of the rotary guides 1 and 2, as observed from a view direction A (shown in FIG. 4A), the maximum allowable usable space for maneuvering the needle holder 6 is an space [2] shown in FIG. 4B. However, the tilted second rotary guide 3 needs not use the entirety of space [2]. Indeed, only half of space [2] can be used because whatever orientation of the needle holder 6 in that half-range of space [2] can also be oriented within the other half-range by using the rotation of the horizontal first rotary guide 1. That is, rotating both the first rotation guide 1 and the second rotation guide 3 allows the positioning of the needle holder 6 any part of the maximum allowable space [2]; this was already illustrated in a more generalized manner in FIG. 3C.

<Second Embodiment>

Figure 5A:
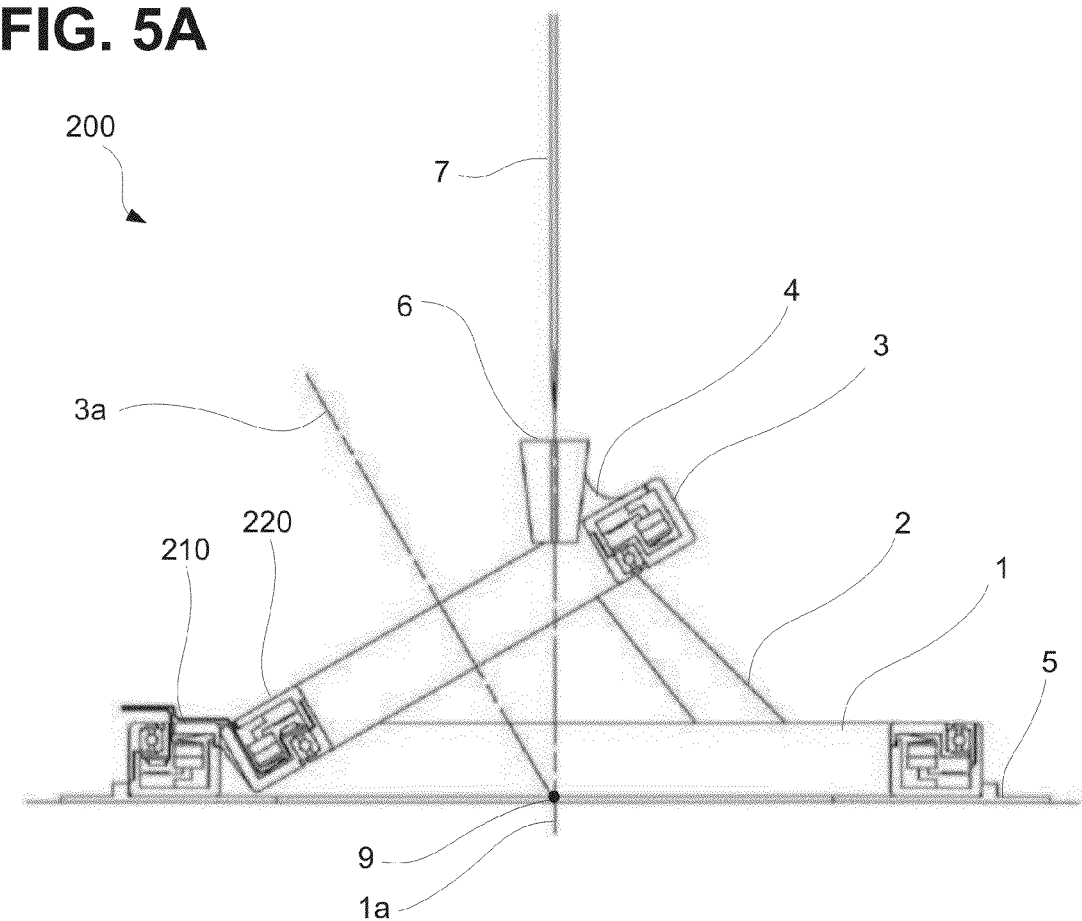
FIGS. 5A and 5B are sectional views of a needle placement manipulator equipped with a motorized actuator, according to a second embodiment.
Figure 5B:
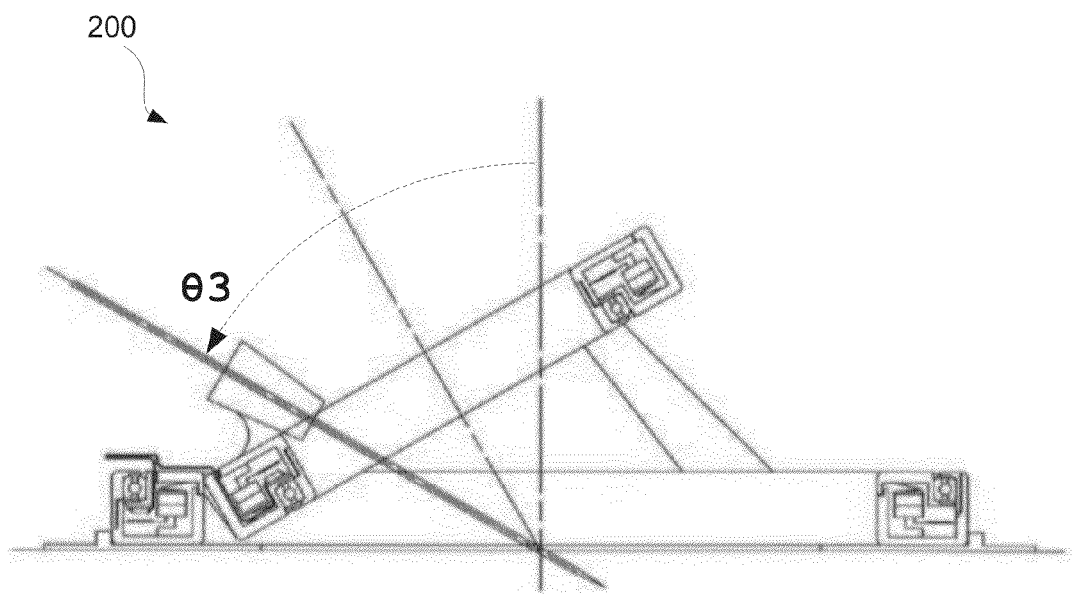

FIGS. 5A and 5B are sectional views of a needle placement manipulator 200, in accordance with a second embodiment. FIG. 6 is a detailed sectional view of the left side of FIG. 5A. The second embodiment is substantially similar to the first embodiment. One notable difference in the needle placement manipulator 200, according to the second embodiment, is that the manipulator 200 includes motorized actuators for the rotation of first and second rotary guides 1 and 3.

Specifically, in this embodiment, the first rotary guide 1 now includes a rotation drive unit 210, and the second rotary guide 2 includes a rotation drive unit 220. In the first rotary guide 1, the rotation drive unit 210 comprises a piezoelectric actuator 11, a rotary slider 12, a ball-bearing 13, a screw part 14, a pressurized means 15, a first electric cable 16, a position sensor 17, a rotary scale 18, a second electric cable 19, and an external casing 1.1 and internal casing 1.2.

Figure 6A:
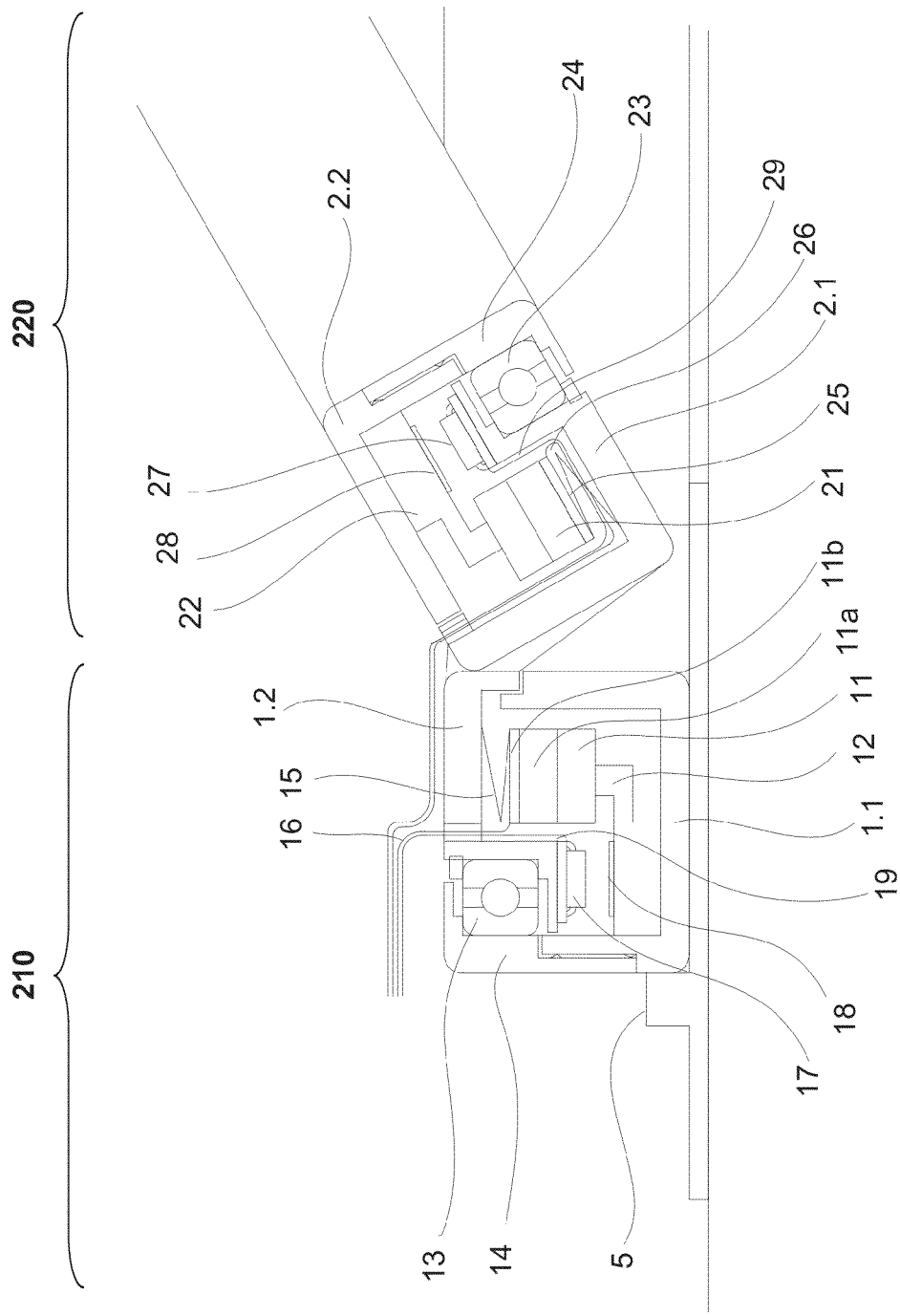
FIG. 6A illustrates a detailed sectional view of the left side of FIG. 5A.

As shown in FIG. 6A, the piezoelectric actuator 11 comprises a vibrator body 11a and piezoelectric material 11b. The piezoelectric material 11b is fixed to vibrator body 11a with adhesive. The piezoelectric material 11b embeds a plurality of electrodes (not drawn) which apply electric voltage to the piezoelectric material 11b. Piezoelectric actuator 11 is supported through pressurized means 15 to internal casing 1.2 of the rotary guide 1. External casing 1.1 and internal casing 1.2 are relatively rotatable by bearing 13 which is fixed by the screw part 14. The rotary slider 12 is fixed to external casing 1.1. The piezoelectric actuator 11 and rotary slider 12 are pressurized against each other by pressurized means 15. Applying a driving voltage to electrodes of piezoelectric material 11b through electric cable 16, the vibrator body 11a vibrates and the rotary slider 12 is driven by frictional force between actuator 11 and rotary slider 12. Specifically, piezoelectric material, such as barium titanate or lead zirconate titanate, which expands or shrinks in volume by applying an electric voltage thereto may be used. Internal casing 1.2 is driven by the piezoelectric actuator. In the present embodiment, the pressurized means 15 can be implemented by a coil spring, but it can also be a pressure plate, a wave washer spring, or like pressing devices. The piezoelectric actuator 11 may, in some applications, be exchanged for an electrostrictive actuator.

The position sensor 17 is attached to the surface of internal casing 1.2. Rotary scale 18 is mechanically attached to the surface of the rotary slider 12. Electric power supply to position sensor 17 and detected signals thereof are transferred by electric cable 19. Position sensor 17 detects relative rotational position by detecting the rotary scale 18.

In the second rotary guide 2, the rotation drive unit 220 is substantially similar to rotation drive unit 210. Rotation drive unit 220 comprises a piezoelectric actuator 21, a rotary slider 22, a bearing 23, a screw part 24, a pressurized means 25, a first electric cable 26, a position sensor 27, a rotary scale 28, a second electric cable 29, an external casing 2.1 and internal casing 2.2.

Structure of second rotary guide 2 is similar to first rotary guide 1. A structural difference of second rotary guide 2 from first rotary guide 1 is that the function of external casing 2.1 and internal casing 2.2 are interchanged. The piezoelectric actuator 21 is supported through the pressurized means 25 to external casing 2.1. Position sensor 27 is also fixed to external casing 2.1. Rotary slider 22 is fixed to internal casing 2.2.

In the embodiment shown in FIG. 6A, only one position sensor and one actuator for each of the guides 1 and 3 have been shown for the sake of clarity in the illustration. The position sensors and actuators may be installed more than one to each of the guides. In this manner, additional position sensors and actuators can be provided to be used as backup or supplemental to the first ones in various instances of the operation of the manipulator to increase reliability, stability and precision of the manipulator.

As in the first embodiment, the manipulator 200 of the second embodiment is constrained to operate needle positioning within a maximum available space [2] determined by the tilted arrangement of the second rotary guide 3 with respect to the first rotary guide 1, as discussed in reference to FIGS. 4A and 4B. With such arrangement, as illustrated in FIG. 5B, the needle manipulator 200 is configured to position the needle at any position between a substantially perpendicular position (where θ=0 degrees) and a maximum angle of inclination θ3 determined by equation (1).

<Available Exemplary Materials for Rotation Units 210 or 220>

Certain Available Exemplary Materials for rotation drive units 210 or 220 may be selected, as follows:

Vibrator body: non-magnetic metal, ceramics (e.g., alumina, zirconia, partially stabilized zirconia), and other non-magnetic materials;

Rotary slider: engineering plastic material such as polytetrafluoroethylene (PTFE), polyether ether ketone (PEEK), polyimide (PI), Polyamide-imide (PAI), Polyphenylene sulfide (PPS), fiber reinforced plastic material such as carbon filled, glass fiber filled or ceramics material;

Bearing: ceramics, plastic, air bearing;

Position sensor: optical-electrical type, fully optical (optical fiber);

Scale: print on plastic sheet, molded plastic, glass grating, etc.;

Position sensor and index scale may be implemented in various different manners. For example, these can be implemented by micro optical encoders. Alternatively, the position sensor can be implemented as a purely optical sensor, by using optical fibers.

Figure 6B:
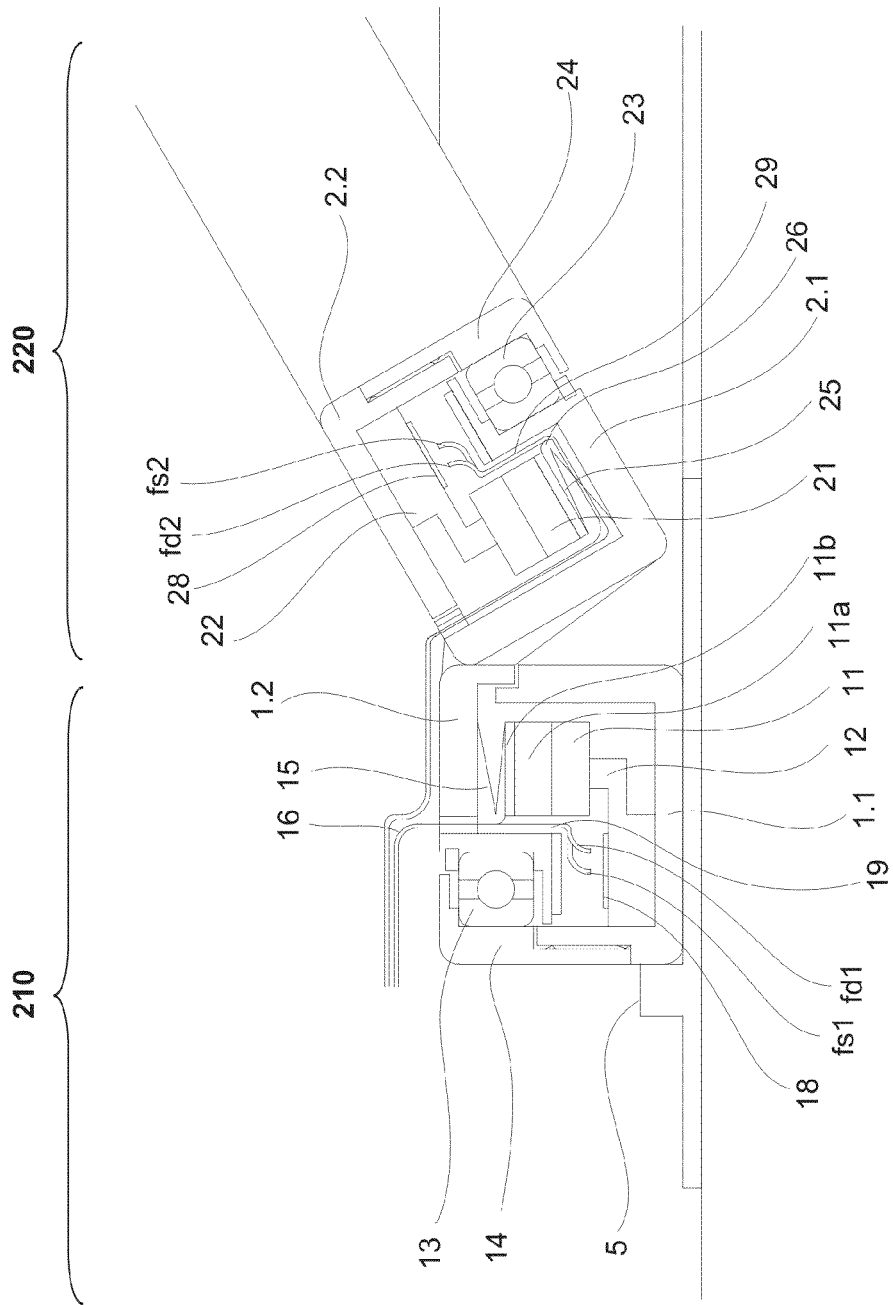
FIG. 6B illustrates a detailed sectional view of the left side of FIG. 5A using optical fibers.

FIG. 6B illustrates a variation of the second embodiment where, in the first rotation drive unit 210, a light source fiber fs1 delivers light to the rotary scale 18 and a collecting fiber fd1 is used to detect light reflected from the rotary scale 18. Similarly, in the second rotation drive unit 220, a light source fiber fs2 delivers light to the rotary scale 28 and a collecting fiber fd2 is used to detect light reflected from the rotary scale 28. The use of optical fibers may be particularly desirable to avoid the use of electrical wiring for minimizing noise and interference in the MRI system, in particular to avoid interference with RF-pulse signals.

Advantageously, in the second embodiment, accurate positioning up to an order of microns can be implemented by the use of optical rotary position sensors and piezoelectric actuators. Accurate positioning is available by piezoelectric actuator and feedback signaling, which can be automated by controllers operated with programmed algorithms. At least two piezoelectric vibrators and two position sensors are arranged into the parts which are not relatively movable. Arranging the piezoelectric vibrators and position sensors within non-movable parts permits that all electric cables can be tied into one bundle. Therefore, shielding of electric cables to decrease noises which MRI receives can be simplified. The manipulator can be moved without entangling of cables, so arrangement of electric cables can be simplified.

Conventionally, prior to every needle incision operation, the needle holder 6 and the base body 5 must be sterilized because they are touched by clinician and patient. In accordance with embodiments disclosed herein, base body 5 and other parts fixed to external casing 1.1 can be made of disposable and recyclable materials, such as plastic. In this manner, these parts can be disposable in one clinical procedure. The needle holder 6 and the internal casing 2.2 can also be made of disposable materials. In this manner, the characteristics of piezoelectric actuators are stable because the friction surface of the rotary slider which faces to piezoelectric vibrator is a new surface in each clinical procedure.

Figure 7A:
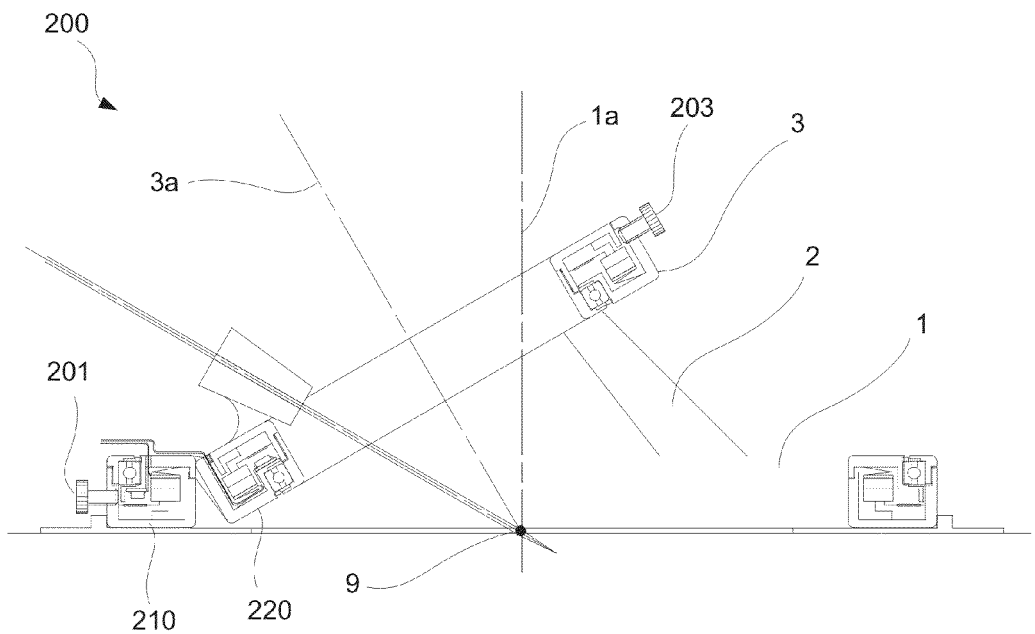
FIG. 7A illustrates an example of a motorized needle manipulator including set screws for locking the rotational guides in a stopped position, according to a modification of the second embodiment.

Arranging piezoelectric actuators and rotary sliders to be ring or arc shape to be fit to the circular shape of rotary guides, the manipulator can be motorized to be automated, and yet maintain a small size. Holding torque of piezoelectric actuator stabilizes the manipulator in a stop state. Alternatively, stop screws as those provided in the first embodiment may be arranged within the external casing 1.1 so that a clinician may optionally secure the rotating guides with the screws, in addition to the piezoelectric actuator stop. FIG. 7A illustrates an example of a motorized manipulator 200, in accordance with a modification of the second embodiment. In FIG. 7A, set screws 201 and 203 are used as a locking mechanism for locking the rotational guides 1 and 3, respectively, in a stopped position. Stop set screws can be advantageous in a case where there is a possibility of unexpected power supply or rotating force being applied to the rotary guides, while the piezoelectric actuator keeps its stopped position only by friction, for example.

Figure 7B:
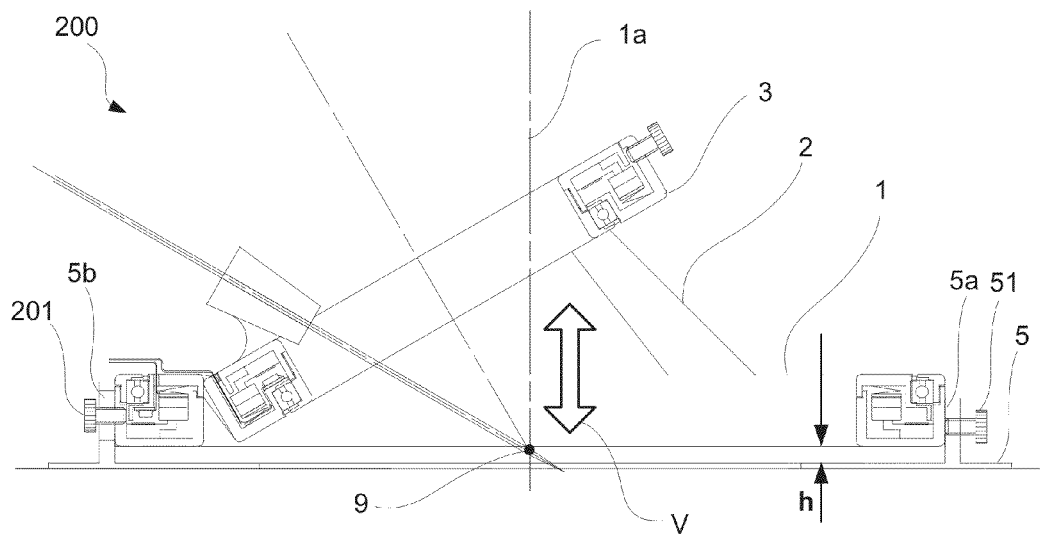
FIG. 7B illustrates an example of a motorized needle manipulator in which the base body includes a sliding portion to adjust a height of the crossing point, according to a further modification of the second embodiment.

FIG. 7B illustrates a further modification to the needle manipulator 200 in accordance with the second embodiment. In FIG. 7B, the base body 5 includes a fitting and sliding portion 5a in which the first rotary guide 1 is disposed (fitted) with a certain degree of tolerance, such that the first rotary guide 1 slides in a vertical direction V perpendicular to the bottom surface of base body 5. When the first rotary guide 1 is allowed to slide in the vertical direction V (perpendicularly) with respect to the bottom surface of base body 5, a distance h (height) between the bottom surface of the base body 5 and the first rotary guide 1 can be selectively adjusted. Once the rotary guide 1 is located at a desired distance or height h with respect to the bottom surface of base body 5, the first rotary guide 1 is locked in place by a height locking mechanism, such as a set screw 51. In this manner, it is possible to adjust the position (height or distance) of the crossing point 9 with respect to a target surface (e.g., the skin 8 of a patient's body). In this embodiment, even when the position (height) of crossing point 9 is changed along the axis 1a of the first rotary guide 1, the rotational axis 1a of the first rotary guide 1, rotational axis 3a of the second rotary guide 3, and the needle holder axis 6a still cross each other at a single crossing point 9. Advantageously, the crossing point 9 can be adjusted to the target surface to, for example, accommodate the various shapes of a patient's body parts. In this embodiment, it should be noted, that when the rotary guide 3 is made to slide vertically with respect to the base body 5, the set screw 201 will also slide in the V direction together with the rotary guide 1. To that end, the sliding portion 5a of base body 5 should be modified to include a hollow portion 5b to allow vertical displacement of the set screw 201.

<Third Embodiment>

A third embodiment is now described with respect to FIGS. 8A, 8B and 9. A needle manipulator 300, in accordance with the third embodiment is substantially similar to the manipulator 100 of the first embodiment in that needle positioning is effected by manually rotating the rotary guides 1 and 3. A notable difference in the third embodiment, in contrast to the first one, is that the manipulator 300 includes an attached RF-coil.

Figure 9A:
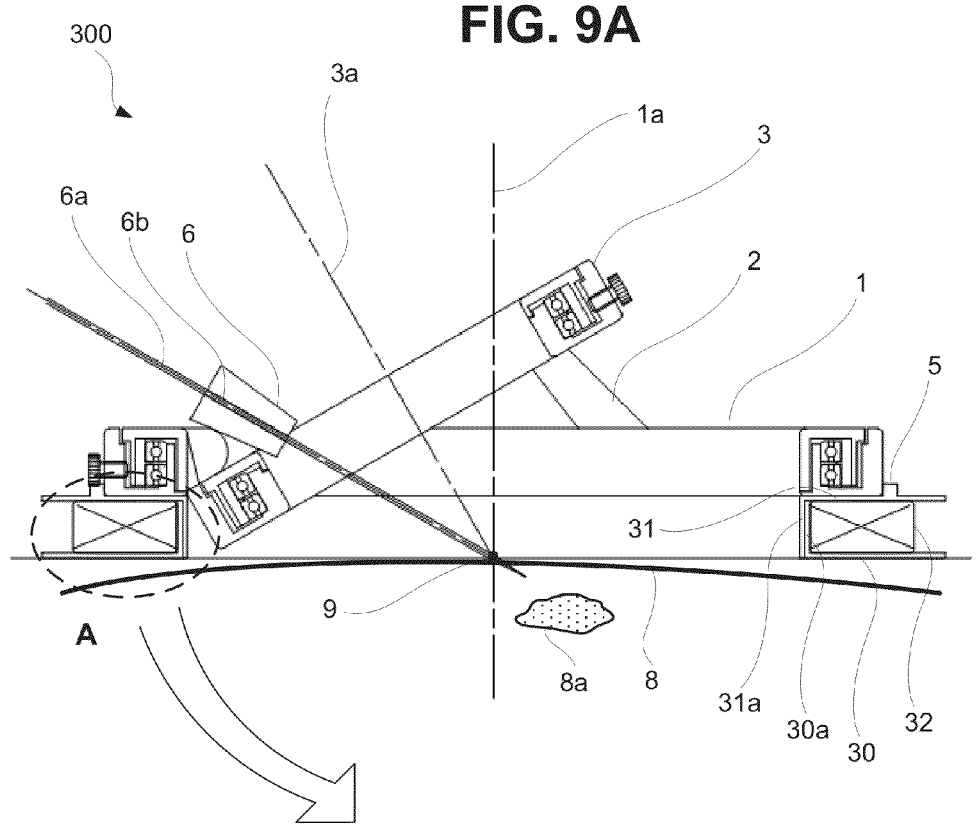
FIG. 9A illustrates a sectional view of the needle manipulator cut along a vertical plane H-H, according to the third embodiment.

Specifically, FIG. 8A is a perspective view of manipulator 300 and FIG. 8B is a perspective view of the manipulator 300 showing a vertical cut along plane H-H, in accordance with third embodiment. FIG. 9A is a sectional view of the manipulator 300 cut along the vertical plane H-H, according to the third embodiment. The needle manipulator 300 of the present embodiment may be particularly suitable for use in MRI-guided percutaneous interventions. In this embodiment, the manipulator 300 includes attachments for an RF-coil which is used in a MRI-scanner. The structure for positioning needle 7 is basically the same as the one described in first embodiment.

As illustrated in FIG. 8A, the manipulator 300 includes a first attachment 30 and a second attachment 31 to fix the manipulator 300 to a single loop RF-coil 32. The first attachment 30 is placed directly on a patient such that a bottom surface of the first attachment 30 rests on the patient's skin, for example. The needle manipulator 300 includes a plurality of fiducial markers 10a, 10b, 10c and 10d in the first rotary guide 1 and fiducial markers 10e, 10f, 10g through 10h (10e not shown) on the second rotary guide 3, as described in the first embodiment. In addition, at least the first attachment 30 includes fiducial markers 33a, 33b, 33c and 33d (markers 33c and 33d are not seen in FIG. 8A). Since the first attachment 30 remains fixed to the body of the subject under examination, the fiducial markers 33a-33d serve as a reference, so that needle position and orientation can be tracked with fiducial markers located on either one or both of the guides (e.g., fiducial markers 10a-10h).

FIG. 8B illustrates a perspective view of the manipulator 300 mounted onto RF-coil 32 in which a sectional cut along vertical plane H-H is performed. FIG. 9A illustrates a sectional view of the needle placement manipulator cut along a vertical plane H-H, according to the third embodiment. The first attachment 30 includes a flat setting portion on which the RF-coil 32 is set, and a circular projection portion 30a configured to engage with the second attachment 31. Similarly, the second attachment 31 includes a flat setting portion below which the RF-coil is set, and a circular projection portion 31a which engages with the projection portion 30a of the first attachment 30.

As illustrated in FIG. 9A, the single loop RF-coil 32 is placed with the circular projection 30a of attachment 30 going through the opening of the RF-coil 32. The second attachment 31 is fixed to the base body 5 and the circular projection section 31a is disposed at the bottom surface thereof. These two attachments 30 and 31 are configured to be engaged (fitted) by the two circular projections 30a and 31a, respectively, such that the two attachments remain fixed at relative positions while securing the RF-coil 32 therebetween. Fixing the two attachments 30 and 31 at relative positions can be done by one or more set screws (not shown), or by force fitting (pressure), or by one or more air chucks (not shown), or by any other mechanical means that will prevent unexpected movement or dislodging between the two attachments.

Figure 9B:
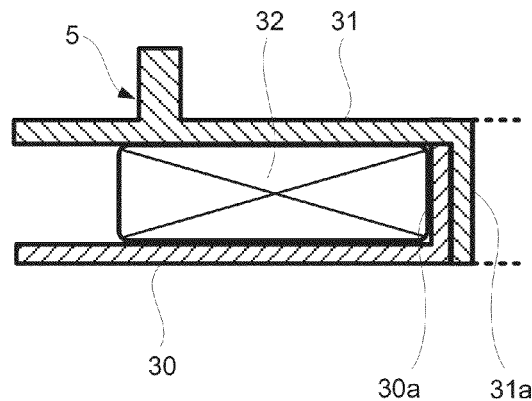
FIG. 9B illustrates a detailed view of section A shown in FIG. 9A where a first attachment 30 engages with a second attachment 31 on an outer surface thereof.
Figure 9C:
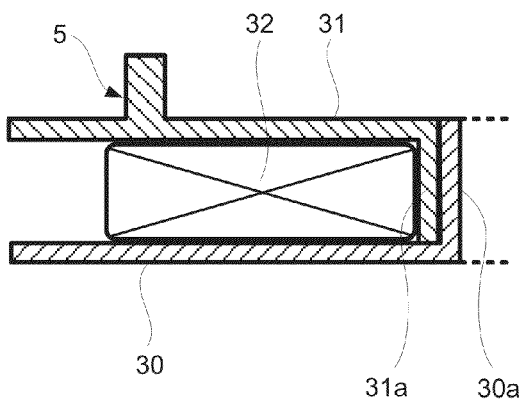
FIG. 9C illustrates a detailed view of section A shown in FIG. 9A where a first attachment 30 engages with a second attachment 31 on an inner surface thereof.

FIG. 9B illustrates a detailed view of section A shown in FIG. 9A where a first attachment 30 engages with a second attachment 31 on an outer surface thereof. FIG. 9C illustrates a detailed view of section A shown in FIG. 9A where a first attachment 30 engages with a second attachment 31 on an inner surface thereof. Regardless of how the two attachments have been joined, the two attachments 30 and 31 are engaged (fitted) into each other by the two circular projections 30a and 31a, respectively, such that the two attachments remain fixed at relative positions while securing the RF-coil 32 therebetween. Notably, as shown in FIGS. 9B and 9C, the second attachment 31 may be integrated into the base body 5. In this manner, the base body 5 and the second attachment 31 are integrally attached as a single mechanical structure. Moreover, the second attachment 31, the based body 5 and the non-movable portion of the first guide 1 can be integrally formed as a single mechanical structure. Making the second attachment 31 an integral part of base body 5, or making the second attachment 31 with base body 5 and part of the first guide 1 an integral structure may facilitate prompt attachment and detachment of the needle manipulator 300 onto the RF-coil 32. However, as described above, the attachment 31 may be removably attached to the base body 5.

Once the two attachments are assembled with the manipulator 300, the axis 1a of the first rotary guide 1, the axis 3a of the second rotary guide 3 and the needle holder axis 6a of the needle holder 6 are arranged to cross at a single crossing point 9. The crossing point 9 is preferably located at the center of gravity of manipulator 300, which should be located at the geometric center of the bottom surface of first attachment 30. Fitting part of circular projections 31a and 30a can be replaced by screw adjustment, so that the crossing point 9 is adjustable with respect to the patient's skin, as shown in FIG. 7B.

If the RF-Coil includes a plurality of openings, like a body matrix coil, the RF-coil attachment 30 is prepared according to the shape of each opening. If the opening of the RF-coil is of a square shape, attachment 30 should be made in a square shape too, and attachment 31 should be made to adapt, on one side, to the shape of the base body 5, and on the other side to the attachment 30.

Figure 10A:
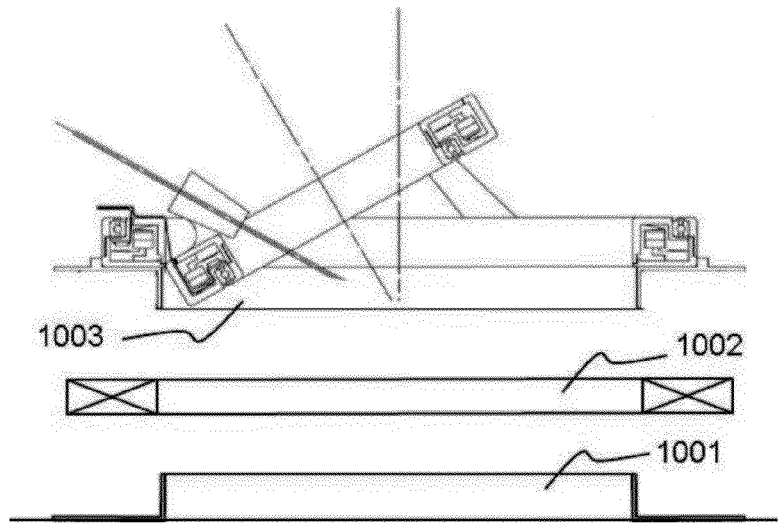
FIGS. 10A, 10B and 10C illustrates an exemplary procedure for attaching and detaching a needle manipulator to an RF-coil with attachments therefor.
Figure 10B:
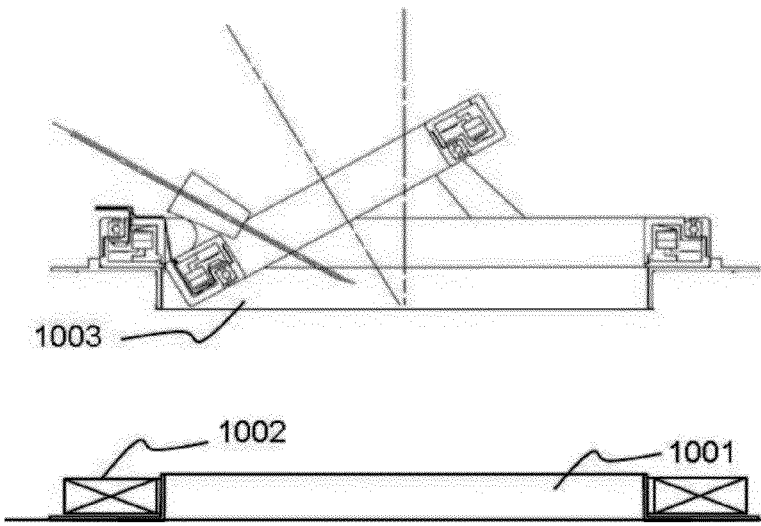
Figure 10C:
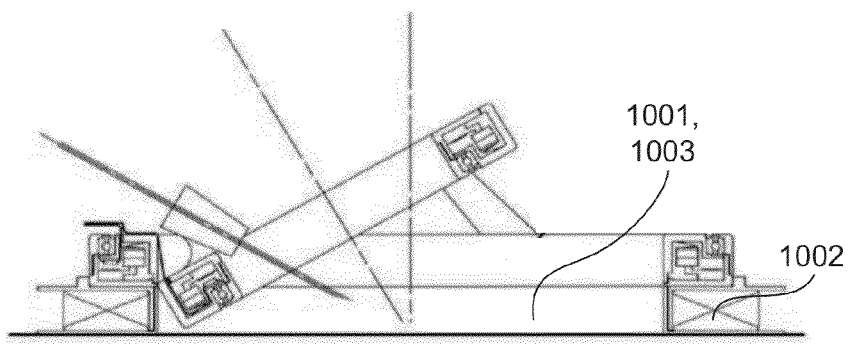
Figure 11:
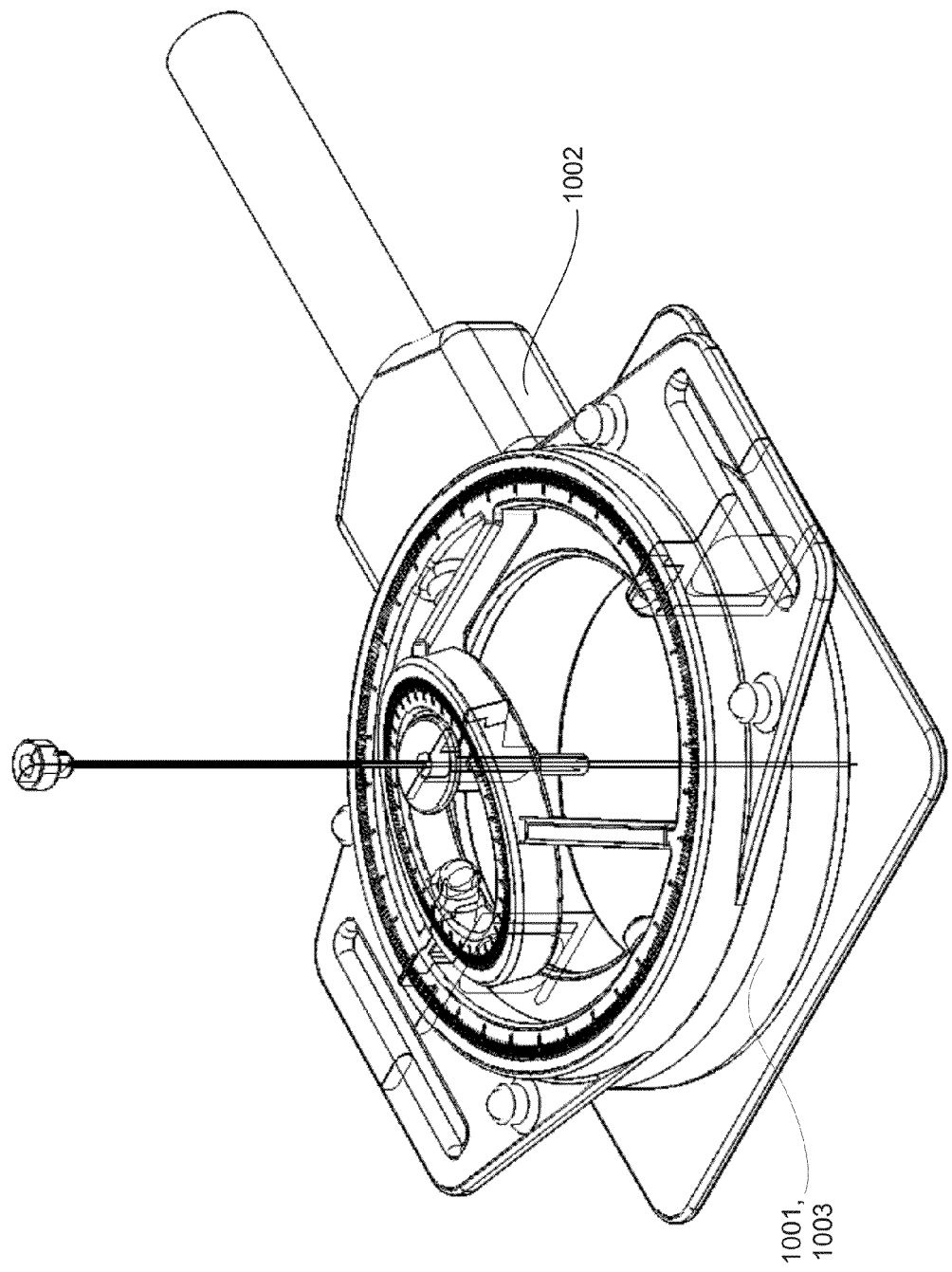
FIG. 11 illustrates a perspective view of the assembled needle manipulator attached to the RF-coil with first and second attachments engaged to each other.

Turning now to FIGS. 10A through 10C, a description is provided of an exemplary procedure for attaching and detaching the manipulator 300 and RF-coil 32 onto a body of a target patient. FIG. 10A shows a first attachment 1001 with an upward protruding ring (protrusion section), a single loop RF-coil 1002, and a second attachment 1003 with a downward protruding ring. In FIG. 10A, the first attachment 1001 with its protruding ring facing upward is first set on a patient (the subject of needle placement), and the second attachment 1003 with the protruding ring facing downward is attached to base body 5 of the needle manipulator. The protruding ring of first attachment 1001 is arranged to engage with the protruding ring of the second attachment 1003. In FIG. 10B, the RF-coil 1002 is set on the first attachment 1001. The opening of RF-coil 1002 is loosely fit around the protruding ring of the first attachment 1001, so that the RF-coil 1002 can be rotated or moved to adjust the positioning of cabling and other parts (not shown in the figure). In FIG. 10C, the needle manipulator unit is set onto the first attachment 1001. The second attachment 1003, which is the part protruding downward from the needle manipulator unit, engages firmly with the first attachment 1001 so that needle position and orientation with respect to the patient can be accurately known, by tracking the fiducial markers. FIG. 11 is a perspective view of the assembled needle manipulator attached to the RF-coil 1002 and the first and second attachments 1001 and 1003.

Certain Advantages in the third embodiment are that the opening of RF-coil and the manipulator's opening (space through which the needle is inserted) are made to coincide with each other. In this manner, the opening can be advantageously utilized for a clinician's access to entry point (incision point) of a patient's skin. The RF-coil 32 and manipulator 300 are removably combined into one unit, so that clinical procedure could be simple.

<Fourth Embodiment>

Figure 12:
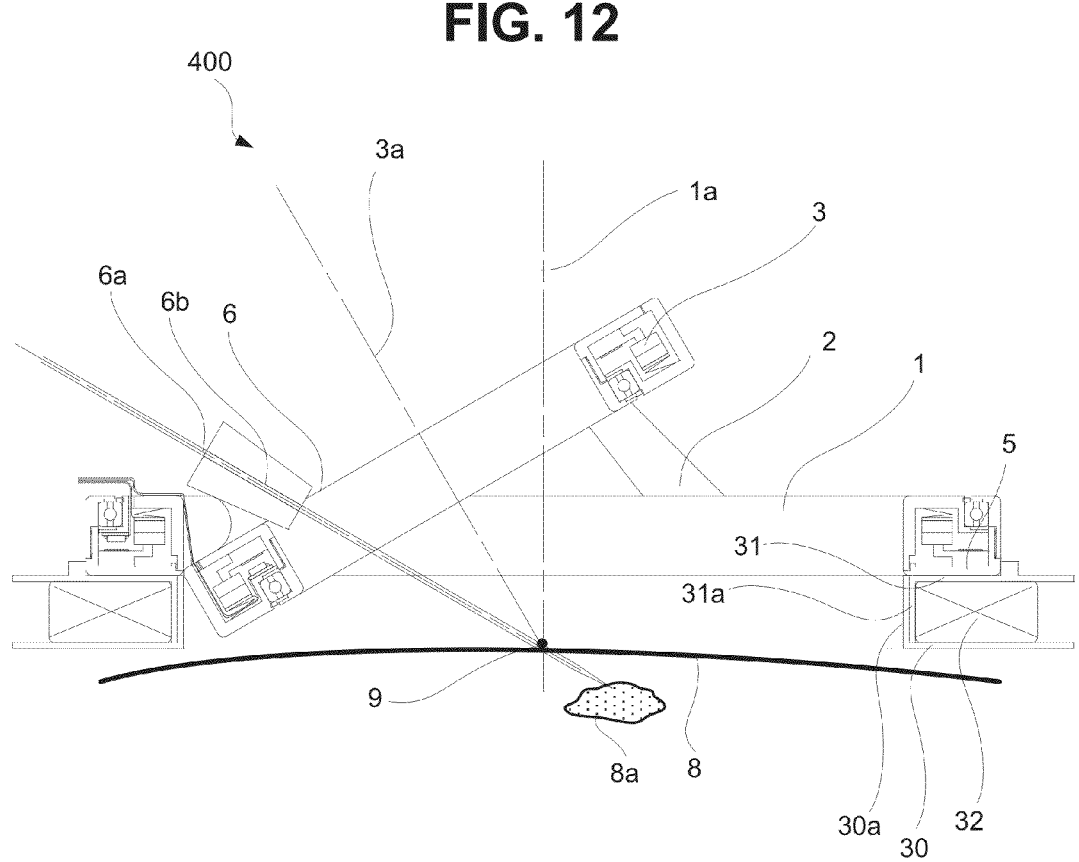
FIG. 12 illustrates a sectional view of a motorized needle manipulator attached to an RF-coil, in accordance with the fourth embodiment.

A fourth embodiment is now described with respect to FIG. 12. A needle manipulator 400, in accordance with the fourth embodiment is substantially similar to the manipulator 200 described above in reference to the second embodiment. A notable difference in the fourth embodiment is that the needle manipulator 400 includes motorized rotational guides 1 and 3, and an attached to RF-coil 32.

Needle positioning in the manipulator 400 of the forth embodiment is automated with piezoelectric actuators and optical sensors. In the present embodiment, a second attachment 31 and the base body 5 can be combined into a single body.

In this manner, RF-Coil's opening and manipulator's opening are made to coincide with each other and utilized for clinician's access to entry point of patient's skin. The positioning accuracy of the manipulator with respect to the subject of the needle placement is improved by directly positioning the first attachment to the patient and the capability of attaching the manipulator to the first attachment with high repeatability. The piezoelectric actuator can guarantee precise positioning and steady fixation (stop); this prevents movement of the manipulator 400 even when movement of the patient occurs. In addition, in an automated robotic application, the actuators can be controlled by a controller (CPU) with programmed algorithms designed so that automatic position adjustment occurs in response to patient movement.

<Fifth Embodiment>

Figure 13:
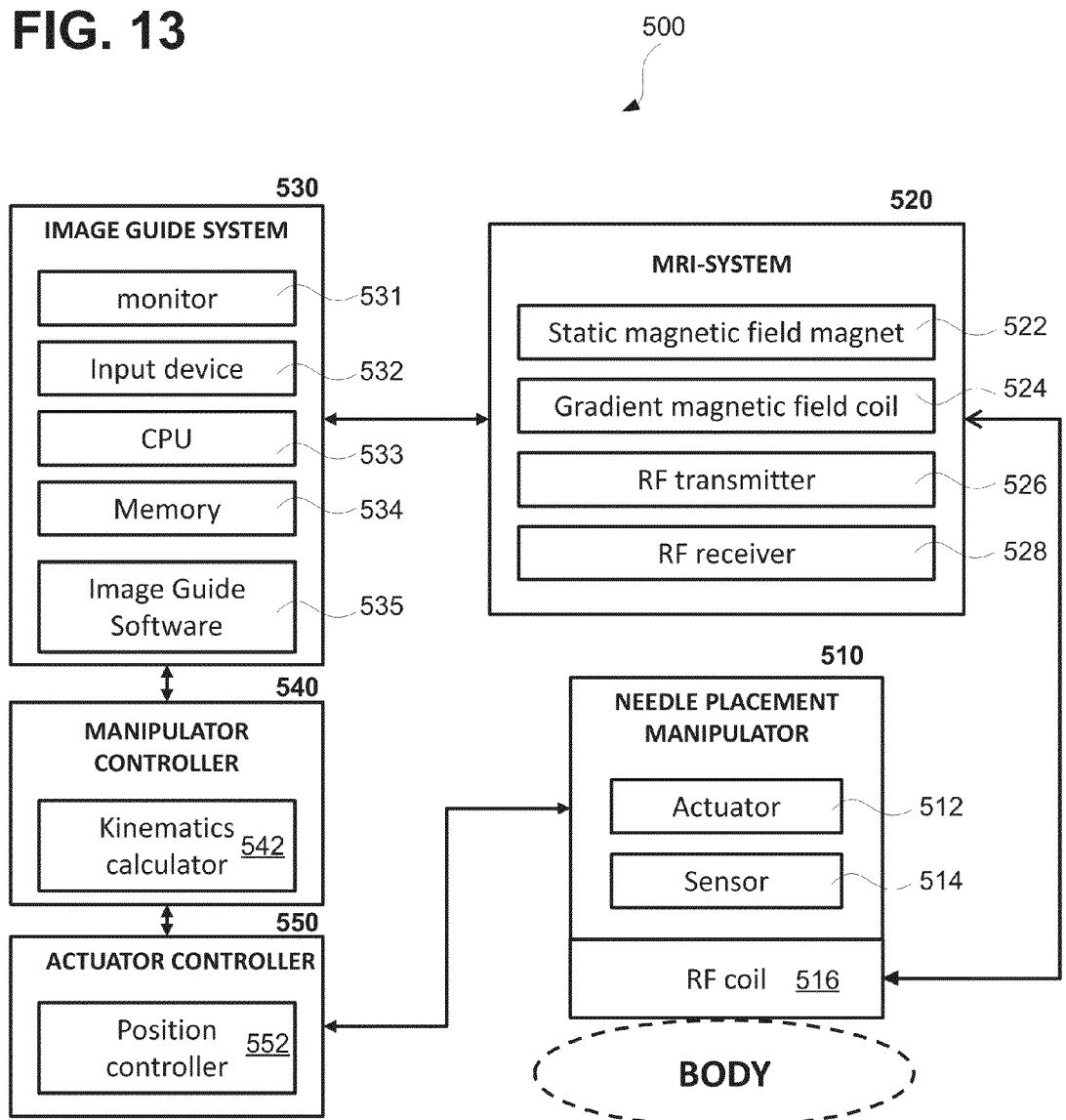
FIG. 13 illustrates a block diagram of an automated image-guided needle positioning system which includes a needle placement manipulator.

FIG. 13 illustrates block diagram of an automated image-guided needle positioning system 500 which includes a motorized manipulator, and can be programmed for automatic (e.g., remote or robotic) manipulation, in accordance with a fifth embodiment. FIG. 13 is a block diagram of the image-guided needle positioning system 500. In accordance with present embodiment, the block diagram shows a function performed by each block included in the system 500. Each function may be implemented purely in hardware and/or a combination of software and hardware.

An image guided needle positioning system 500 includes namely the following main functional blocks: a needle placement manipulator 510, an MRI-system 520, image guide system 530, a manipulator controller 540, and an actuator controller 550. All of the functional blocks are interconnected by circuit or network connectivity. Some of the blocks may be integrated into a single block provided that he combined block still performs the functionally of each block. The needle placement manipulator 510 corresponds to any of the first or second embodiments disclosed herein, as long as an actuator 512 and a sensor 514 can be implemented within the manipulator. The needle placement manipulator 510 including the RF coil 516 corresponds to any of the third and fourth embodiments disclosed herein.

The MRI guide system 530 includes an image monitor (image display) 531, an input device module 532 (e.g., keyboard, mouse, touchpad, etc.), a central processing unit (CPU) implemented by one or more microprocessors, hardware memory 534 (volatile and non-volatile memory and storage devices, such as hard drives may be included), and an Image Guide Software module 535. The image guide software module 535 includes, among other things, programmed algorithms to communicate and control each of the other functional blocks. An example of such image guided application is described by Song et al., in a non-patent literature article entitled "Biopsy Needle Artifact Localization in MRI-guided Robotic Transrectal Prostate Intervention," IEEE transactions on Biomedical Engineering, July 2012.

Image guide system 530 acquires images of a target patient or body-part thereof, of the fiducial markers of in the manipulator and RF-coil base (see, e.g., FIG. 8), and of the needle 7. The manipulator controller 540 communicates with actuator controller 550 for needle positioning. Actuator controller 550 drives piezoelectric actuator 512 or USM (ultrasonic) motor and controls the driving with position sensor 514 in closed-loop control. Kinematics calculator 542 translates the signals from the image guide system 530 into control signals for the actuator controller 550. Actuator controller 550 is implemented in hardware for controlling an actuator (e.g., piezoelectric actuator or USM motor). Position controller 552 may be implemented in software and/or hardware. The position controller 552 calculates a control amount for the actuator 512 so that the needle moves in a target orientation angle based on signal output from a position sensor 514.

In the case of operating under the magnetic field of an MR-based modality (MRI system 520), the static magnetic field magnet 522 generates a static magnetic field in the imaging space. The gradient coil 524 generates a gradient magnetic field in the X-axis direction, a gradient magnetic field in the Y-axis direction and a gradient magnetic field in the Z-axis direction in the imaging space.

An RF transmitter 526 outputs RF pulses (RF current pulses) to the RF coil 516. The RF coil 516 transmits the RF pulses to the human body. The RF coil receives an MR signal generated due to excited nuclear spin inside the human body according to the RF pulse. An RF receiver 528 detects the MR signal. Then, the detected data or a signal based on the detected data is input into an image guide system 530. Volumetric MRI scans can confirm the position and orientation of the needle's tip, based on fixed reference fiducials (e.g., disposed on the RF-coil attachments) and movable fiducials disposed on at least one of the rotary guides. Forward Kinematic Mapping (FKM) can be implemented in the position controller 552 to iteratively drive the needle to a desired target position and to even compensate for positional errors. It is envisioned, for example, an arrangement where, for every needle incision, the position of the manipulator and patient can be registered with respect to the coordinates of the MRI system. During a needle incision procedure, the position of the tip of the needle is also registered with respect to the manipulator, the patient and the MRI system. Then a forward kinematic algorithm performs calculations for controlling the manipulator and updating the position and orientation of the tip of the needle. To ensure precision of needle placement, a safety routine that continuously compensates for needle artifacts can be added to the algorithm.

<Other Embodiments and Modifications>

In the embodiments disclosed above, various combinations and modifications will be readily evident to persons having ordinary skill in the art. As discussed above with respect to FIGS. 4A and 4B, for example, the needle manipulator may be modified to include a second rotary guide 3 having a diameter larger than a diameter of the first rotary guide 1. This modification can allow for the second rotary guide 3 to be placed outside of the first rotary guide 1 instead of inside, as shown in all of the first to fourth embodiments. In addition, although the third to fifth embodiments are directed to MRI-based image guided needle manipulators, the needle manipulators disclosed herein may be applicable to other imaging modalities, such as ultrasound, mammography, computed tomography (CT) and the like. When applied to other modalities, the fiducial markers need not be readable by MRI-scanners as disclosed above. Instead, the fiduciary markers can be modified to conform to the specific imaging modality, or can be removed.

In each of the first to fourth embodiments, the first rotary guide 1 is supported by the base body 5 and connects to a first rotation body 2. The second rotary guide 3 is supported by the first rotation body 2 at a slated angle with respect to the first rotary guide 1. The first rotation body 2 may be of a fixed height it can change in height, such that the second rotary guide 3 can be positioned from substantially parallel to substantially perpendicular to the first rotary guide 1. In this manner, positioning of a needle by the needle holder 6 can apply to other than the maximum angle of rotation and optimal rotation space discussed above.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A needle placement manipulator comprising:
 a first ring shaped rotary guide;
 a first rotation body which is fixed to said first ring shaped rotary guide;
 a second ring shaped rotary guide attached to the first rotation body, the second ring shaped rotary guide being movable along with the first rotation body;
 a second rotation body which is fixed to said second ring shaped rotary guide;
 a needle holder which is fixed to the second rotation body and holds a needle along an axis, the needle holder being movable along with the second rotation body;
 wherein a rotational axis of the first rotary guide and a rotational axis of the second rotary guide are slanted with respect to each other, and
 wherein the rotational axis of the first rotary guide, the rotational axis of the second rotary guide, and the needle holder axis cross each other at one point.

2. The needle placement manipulator according to claim 1 further comprising:
 a base body which is fixed to the first ring shaped rotary guide.

3. The needle placement manipulator according to claim 2, wherein the base body includes plurality of slits for fastening belts.

4. The needle placement manipulator according to claim 2, wherein the base body has a height adjusting mechanism which includes fitting portion at which the base body is fitted to the rotary guide and can be slided in perpendicular direction to each other, and fixing mean which fix the rotary guides to the base body.

5. The needle placement manipulator according to claim 1, further comprising a fixing mechanism configured to fix rotation of at least one of the rotary guides.

6. The needle placement manipulator according to claim 5, wherein the fixing mechanism includes at least a set-screw.

7. The needle placement manipulator according to claim 5, wherein the fixing mechanism includes at least one air clutch configured to release rotation of at least one of the rotary guides by air-supply.

8. The needle placement manipulator according to claim 1, further comprising at least one fiducial marker arranged in at least one of the base body, the first rotary guide or the second rotary guide.

9. The needle placement manipulator according to claim 1, further comprising a position sensor which detects rotational displacement of at least one of the rotary guides.

10. The needle placement manipulator according to claim 9, wherein the position sensor comprises an optical sensor.

11. The needle placement manipulator according to claim 10, wherein the position sensor comprises an optical fiber cable.

12. The needle placement manipulator according to claim 1, further comprising an actuator arranged to rotate at least one of the rotary guides.

13. The needle placement manipulator according to claim 12, wherein the actuator is actuated by piezoelectric material.

14. The needle placement manipulator according to claim 13, wherein the piezoelectric actuator includes:
a piezoelectric vibrator which includes piezoelectric material,
a rotary slider which contacts piezoelectric vibrator,
a pressurized mechanism which pressurizes the piezoelectric vibrator and rotary slider against each other.

15. The needle placement manipulator according to claim 14, wherein the piezoelectric vibrator and rotary slider are both of a circular ring shape.

16. The needle placement manipulator according to claim 14, wherein the piezoelectric vibrator includes piezoelectric material which expands or shrinks in volume by applying electric voltage thereto, and a vibrator body to which piezoelectric material is fixed.

17. The needle placement manipulator according to claim 16, wherein the vibrator body includes ceramic material comprising at least one of alumina, zirconia and partially stabilized zirconia.

18. The needle placement manipulator according to claim 14, wherein the rotary slider includes resin or plastic material.

19. The needle placement manipulator according to claim 1, wherein the first ring shaped rotary guide includes a first part and a second part movable relatively to each other, and
wherein the first rotation body is fixed to the first part of the first ring shaped rotary guide,
wherein the second ring shaped rotary guide includes a first part and a second part movable relative each other,
wherein the second part is fixed to the first rotation body, and the second rotation body which is fixed to the first part of the second ring shaped rotary guide.

20. The needle placement manipulator according to claim 19, further comprising:
a first piezoelectric vibrator that is arranged in the second parts of the first rotary guide;
a second piezoelectric vibrator that is arranged in the second parts of the second rotary guide;
a first rotary slider which is frictional contact with first piezoelectric vibrator and is arranged in the first parts of the first rotary guide;
a second rotary slider which is in frictional contact with second piezoelectric vibrator and is arranged in the first parts of the second rotary guide.

21. The needle placement manipulator according to claim 1,
wherein the first ring shaped rotary guide which includes first part and second part relatively movable to each other, and the first rotation body which is fixed to said the first part of the first ring shaped rotary guide, and the second ring shaped rotary guide which includes first part and second part relative movable each other, and second part is fixed to said first rotation body, and the second rotation body which is fixed to the first part of the second ring shaped rotary guide,
further comprising:
a first optical light source and detector is arranged into said second parts of the first rotary guide;
a second optical light source and detector is arranged into said second parts of the second rotary guide;
a first optical scale which reflects light of said first optical light source and detected by detector is arranged into said first parts of the first rotary guide; and
a second optical scale which reflects light of said second optical light source and detected by detector is arranged into said first parts of the second rotary guide.

22. The needle placement manipulator according to claim 1,
wherein the first ring shaped rotary guide which includes first part and second part relatively movable to each other, and the first rotation body which is fixed to said the first part of the first ring shaped rotary guide, and the second ring shaped rotary guide which includes first part and second part relative movable each other, and second part is fixed to said first rotation body, and the second rotation body which is fixed to the first part of the second ring shaped rotary guide,
further comprising:
a first piezoelectric vibrator is arranged into said second parts of the first rotary guide;
a first optical light source and detector is arranged into said second parts of the first rotary guide;
a second piezoelectric vibrator is arranged into said second parts of the second rotary guide;
a second optical light source and detector is arranged into said second parts of the second rotary guide;
a first rotary slider which frictionally contact with first piezoelectric vibrator is arranged into said first parts of the first rotary guide;
a first optical scale which reflects light of said first optical light source and detected by detector is arranged into said first parts of the first rotary guide;
a second rotary slider which frictionally contact with second piezoelectric vibrator is arranged into said first parts of the second rotary guide; and
second optical scale which reflects light of said second optical light source and detected by detector is arranged into said first parts of the second rotary guide.

23. The needle placement manipulator according to claim 1, wherein the two rotary guides and rotation body are made of non-metal materials.

24. The needle placement manipulator according to claim 1, wherein one of the first and second ring-shaped rotary guides has a diameter smaller than the other.

25. The needle placement manipulator according to claim 1, wherein the second ring-shaped rotary guide is arranged inside or outside of the first ring-shaped rotary guide.

26. The needle placement manipulator according to claim 1,
wherein the rotational axis of the first ring-shaped rotary guide is inclined with respect to the rotational axis of the second ring-shaped rotary guide at an angle θ1;

wherein the needle holder axis is inclined with respect to the rotational axis of the second ring-shaped rotary guide at an angle θ2; and wherein the needle holder axis is configured to be positioned with respect to the rotational axis of the first ring-shaped rotary guide at an angle $\theta_{needle}$ which satisfies the following condition:

$$0 \leq \theta_{needle} \leq \theta1+\theta2.$$

27. The needle placement manipulator according to claim 1, wherein the rotational axis of the first ring-shaped rotary guide is fixed and the rotational axis of the second ring-shaped rotary guide is configured to precess around the rotational axis of the first ring-shaped rotary guide at an angle θ1, wherein the needle holder axis is configured to rotate around the rotational axis of the second ring-shaped rotary guide at an angle θ2, and wherein the needle holder axis is configured to be positioned with respect to the rotational axis of the first ring-shaped rotary guide at a maximum inclination angle θ3=θ1+θ2.

28. A needle positioning system comprising:
a needle placement manipulator according to claim 1;
a MRI-system configured to acquire an image of a target region of a body, an image of the needle placement manipulator and an image of a needle disposed in the needle placement manipulator;
a image guide system configured to indicate a needle position and orientation with respect to the target region of the body;
a manipulator controller configured to receive the needle position and orientation from the image guide system, and to calculate control signals for driving the needle positioned in the needle placement manipulator to the target region of the body; and
an actuator controller configured to receive the control signals from the manipulator controller, and to supply the control signals to a rotation actuator and a position sensor included in the rotary guides, so as to move the needle positioned in the needle placement manipulator to the target region of the body.

29. The needle positioning system according to claim 28, further comprising:
an RF-coil configured to transmit a probe RF-signal from the MRI-system to the body, and to transmit a response RF-signal from the body to the MRI-system.

30. The needle positioning system according to claim 28, further comprising:
an RF-coil attachment structure configured to attach the needle placement manipulator to an RF-coil,
wherein the needle placement manipulator is configured to be attached to the body with the RF-coil disposed therebetween.

* * * * *